United States Patent
Sahin et al.

(10) Patent No.: US 10,799,534 B2
(45) Date of Patent: Oct. 13, 2020

(54) ENHANCING THE EFFECT OF CAR-ENGINEERED T CELLS BY MEANS OF NUCLEIC ACID VACCINATION

(71) Applicants: BIONTECH CELL & GENE THERAPIES GMBH, Mainz (DE); 03;TRON—TRANSLATIONALE ONKOLOGIE AN DER UNIVERSITÄTSMEDIZIN DER JOHANNES GUTENBERG—UNIVERSITÄT MAINZ GEMEINNÜTZIGE GMBH, Mainz (DE)

(72) Inventors: Ugur Sahin, Mainz (DE); Katharina Reinhard, Mainz-Kostheim (DE); Petra Simon, Mainz (DE); Karolina Anna Mroz, Wiesbaden (DE); Kathleen Hobohm, Kelkheim i. Ts. (DE)

(73) Assignees: BIONTECH CELL & GENE THERAPIES GMBH, Mainz (DE); TRON—TRANSLATIONALE ONKOLOGIE AN DER UNIVERSITÄTSMEDIZIN DER JOHANNES GUTENBERG—UNIVERSITÄT MAINZ GEMEINNÜTZIGE GMBH, Mainz (DE)

( * ) Notice: Subject to any disclaimer, the term of this patent is extended or adjusted under 35 U.S.C. 154(b) by 153 days.

(21) Appl. No.: 15/573,045

(22) PCT Filed: May 9, 2016

(86) PCT No.: PCT/EP2016/060332
§ 371 (c)(1),
(2) Date: Nov. 9, 2017

(87) PCT Pub. No.: WO2016/180778
PCT Pub. Date: Nov. 17, 2016

(65) Prior Publication Data
US 2018/0140634 A1 May 24, 2018

Related U.S. Application Data

(63) Continuation of application No. PCT/EP2015/060356, filed on May 11, 2015.

(51) Int. Cl.
| | | |
|---|---|---|
| A61K 35/17 | (2015.01) | |
| A61K 39/00 | (2006.01) | |
| A61K 9/127 | (2006.01) | |
| A61K 39/395 | (2006.01) | |
| C07K 14/725 | (2006.01) | |
| C07K 16/28 | (2006.01) | |

(52) U.S. Cl.
CPC .............. *A61K 35/17* (2013.01); *A61K 9/127* (2013.01); *A61K 39/0011* (2013.01); *A61K 39/00111* (2018.08); *A61K 39/001112* (2018.08); *A61K 39/001113* (2018.08); *A61K 39/001124* (2018.08); *A61K 39/001168* (2018.08); *A61K 39/001182* (2018.08); *A61K 39/001188* (2018.08); *A61K 39/001195* (2018.08); *A61K 39/39558* (2013.01); *C07K 14/7051* (2013.01); *C07K 16/28* (2013.01); A61K 2039/5156 (2013.01); A61K 2039/5158 (2013.01); A61K 2039/53 (2013.01); A61K 2300/00 (2013.01); C07K 2317/622 (2013.01); C07K 2319/03 (2013.01)

(58) Field of Classification Search
None
See application file for complete search history.

(56) References Cited

U.S. PATENT DOCUMENTS

| | | | |
|---|---|---|---|
| 2013/0309258 A1* | 11/2013 | June ....................... | A61K 35/17 424/184.1 |
| 2014/0099340 A1 | 4/2014 | June et al. | |
| 2016/0058852 A1* | 3/2016 | Ter Meulen ........... | A61K 39/07 424/172.1 |

FOREIGN PATENT DOCUMENTS

| | | |
|---|---|---|
| EP | 3053592 | 8/2016 |
| WO | 2008100598 | 8/2008 |
| WO | 2014144622 | 9/2014 |
| WO | 2015014869 | 2/2015 |
| WO | 2015150327 | 10/2015 |

OTHER PUBLICATIONS

Sahin et al, Nat Rev Drug Discov, Oct. 2014, vol. 3, No. 10, pp. 759-780. (Year: 2014).*
Ly et al, Cancer Res, 2010, vol. 70, Issue 21, pp. 8339-8346. (Year: 2010).*

(Continued)

*Primary Examiner* — Allison M Fox
(74) *Attorney, Agent, or Firm* — McAndrews, Held & Malloy, Ltd.

(57) ABSTRACT

The present invention generally embraces the treatment of diseases by targeting cells expressing an antigen on the cell surface. In particular the invention relates to a method for stimulating, priming and/or expanding in vivo T cells genetically modified to express a chimeric antigen receptor (CAR) targeted to an antigen, comprising contacting the T cells with the antigen or a variant thereof in vivo. In one embodiment, the antigen or variant thereof is provided by administering a nucleic acid encoding the antigen or variant thereof.

Figure 1:
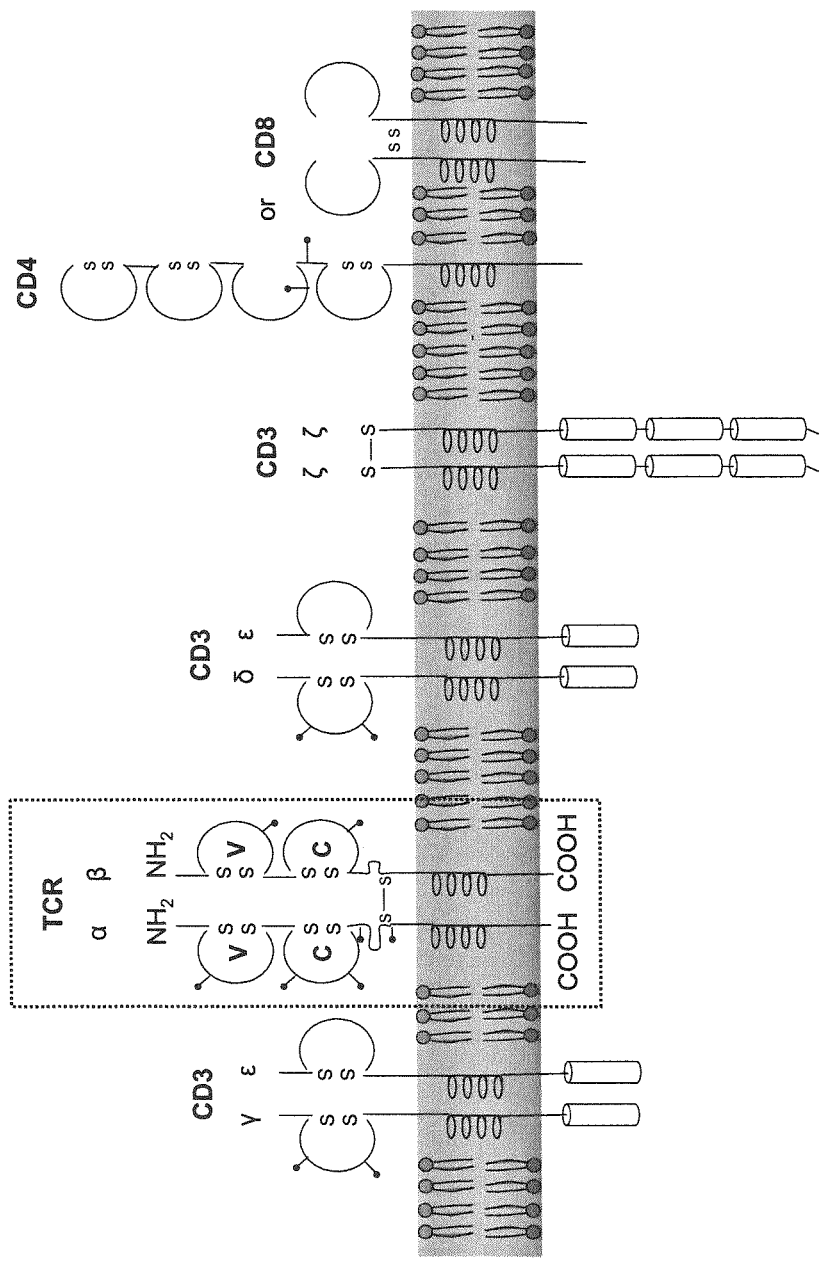

18 Claims, 17 Drawing Sheets
Specification includes a Sequence Listing.

(56) References Cited

OTHER PUBLICATIONS

Lou et al, Cancer Res, 2004, vol. 64, Issue 18, pp. 6783-6790. (Year: 2004).*
Seledtsov et al , Hum Vaccin Immunother Apr. 2015, 11(4): 851-869. (Year: 2015).*
Smith et al., "Impact of a Recombinant Fowlpox Vaccine on the Efficacy of Adoptive Cell Therapy with Tumor Infiltrating Lymphocytes in a Patient with Metastatic Melanoma," J. Immunother, vol. 32, Issue 8, Oct. 2009, pp. 870-874.
Song et al., "A Th1-inducing Adenoviral Vaccine for Boosting Adoptively Transferred T Cells," Molecular Therapy: The American Society of Gene & Cell Therapy, vol. 19, Issue 1, Jan. 2011, pp. 211-217.
Flores et al., "Novel role of hematopoietic stem cells in immunologic rejection of malignant gliomas," OncoImmunology, vol. 4, Issue 3, Mar. 2015, 11 pages.
Wang et al., "CMVpp65 Vaccine Enhances the Antitumor Efficacy of Adoptively Transferred CD19-Redirected CMV-Specific T Cells," Clinical Cancer Research—American Association for Cancer Research, vol. 21, Issue 13, Jul. 1, 2015, pp. 2993-3002.
International Search Report & Written Opinion, dated Jul. 8, 2016, issued by the European Patent Office in connection with PCT/EP2016/060332.

* cited by examiner

A)

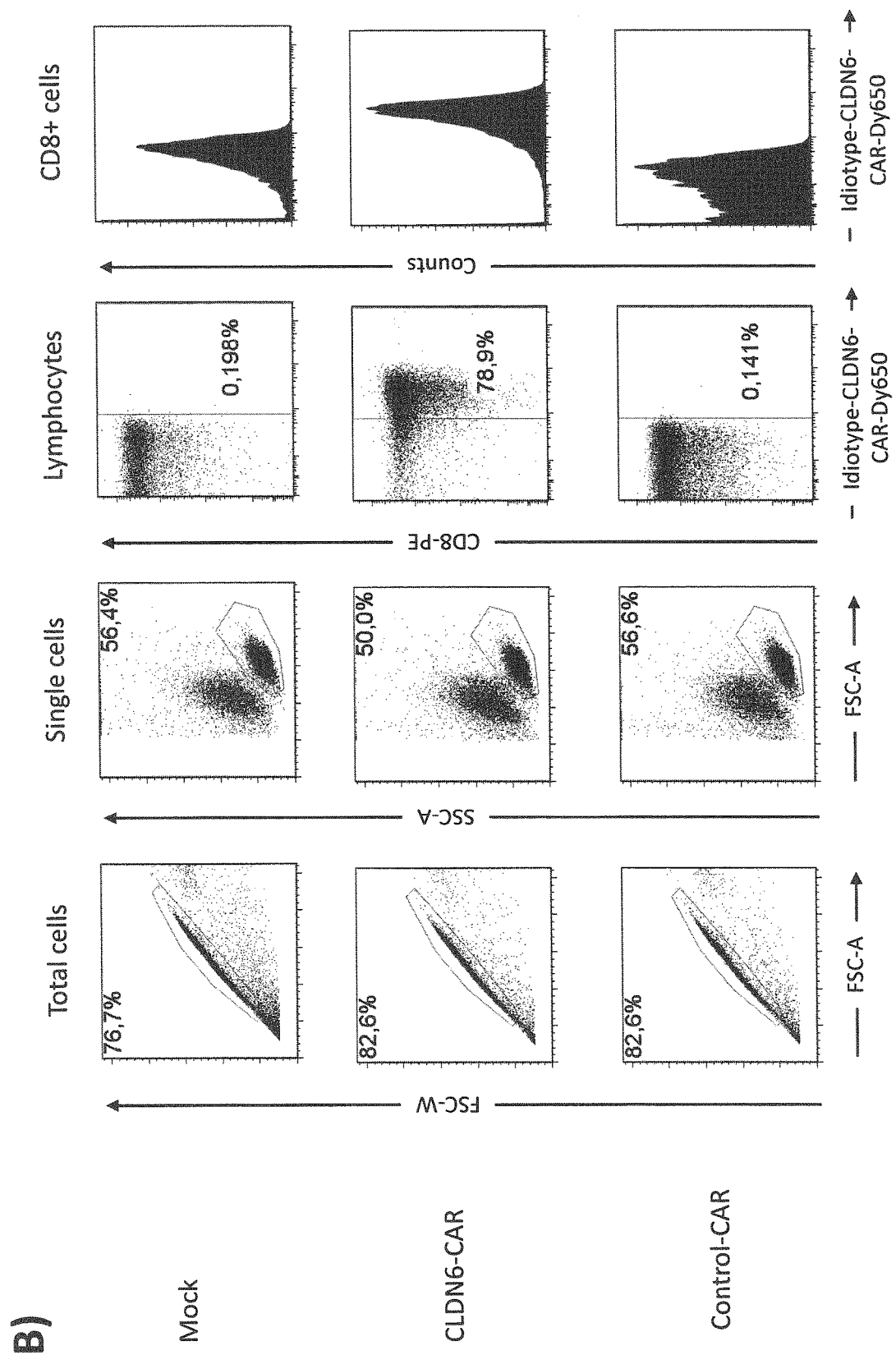

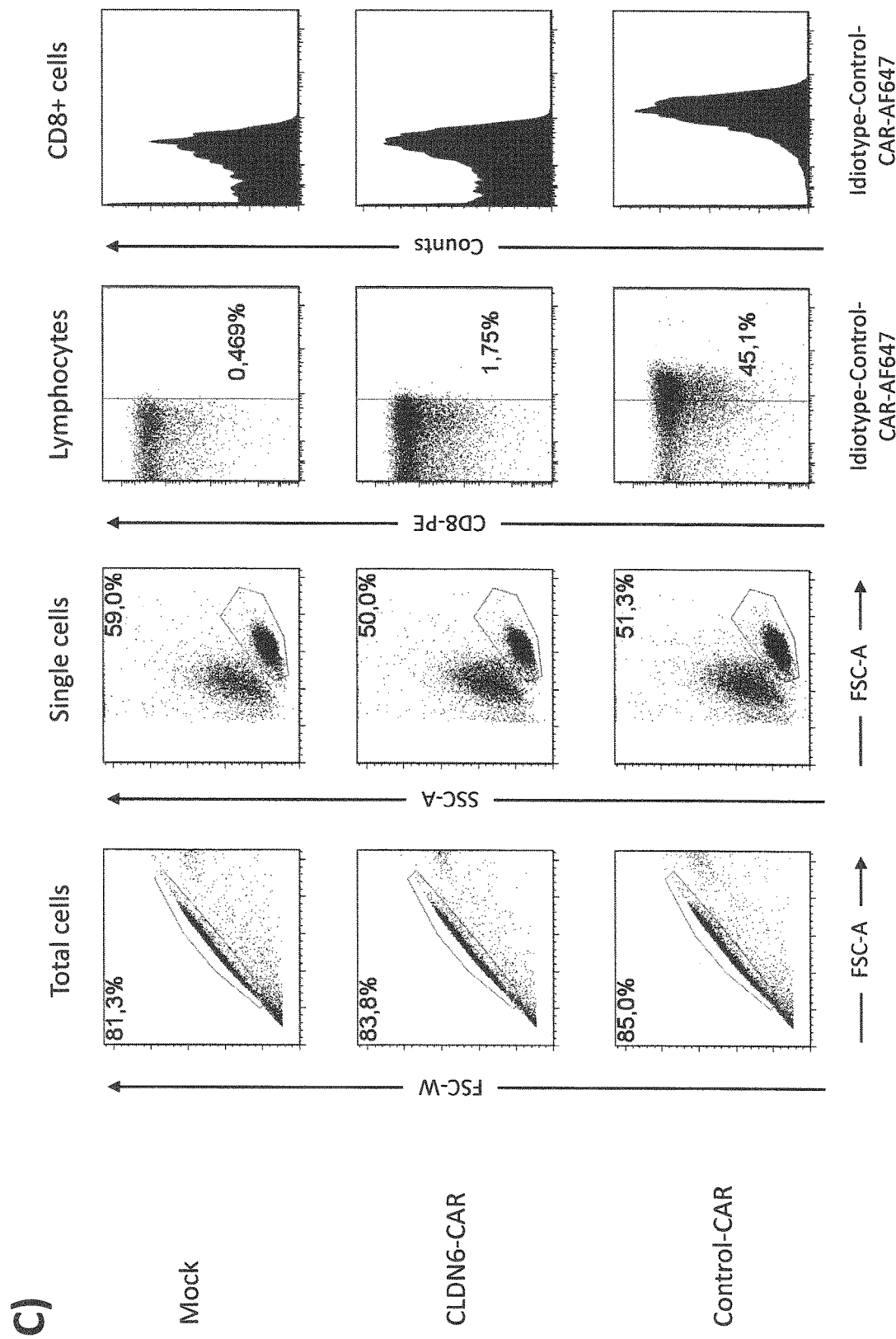

D)

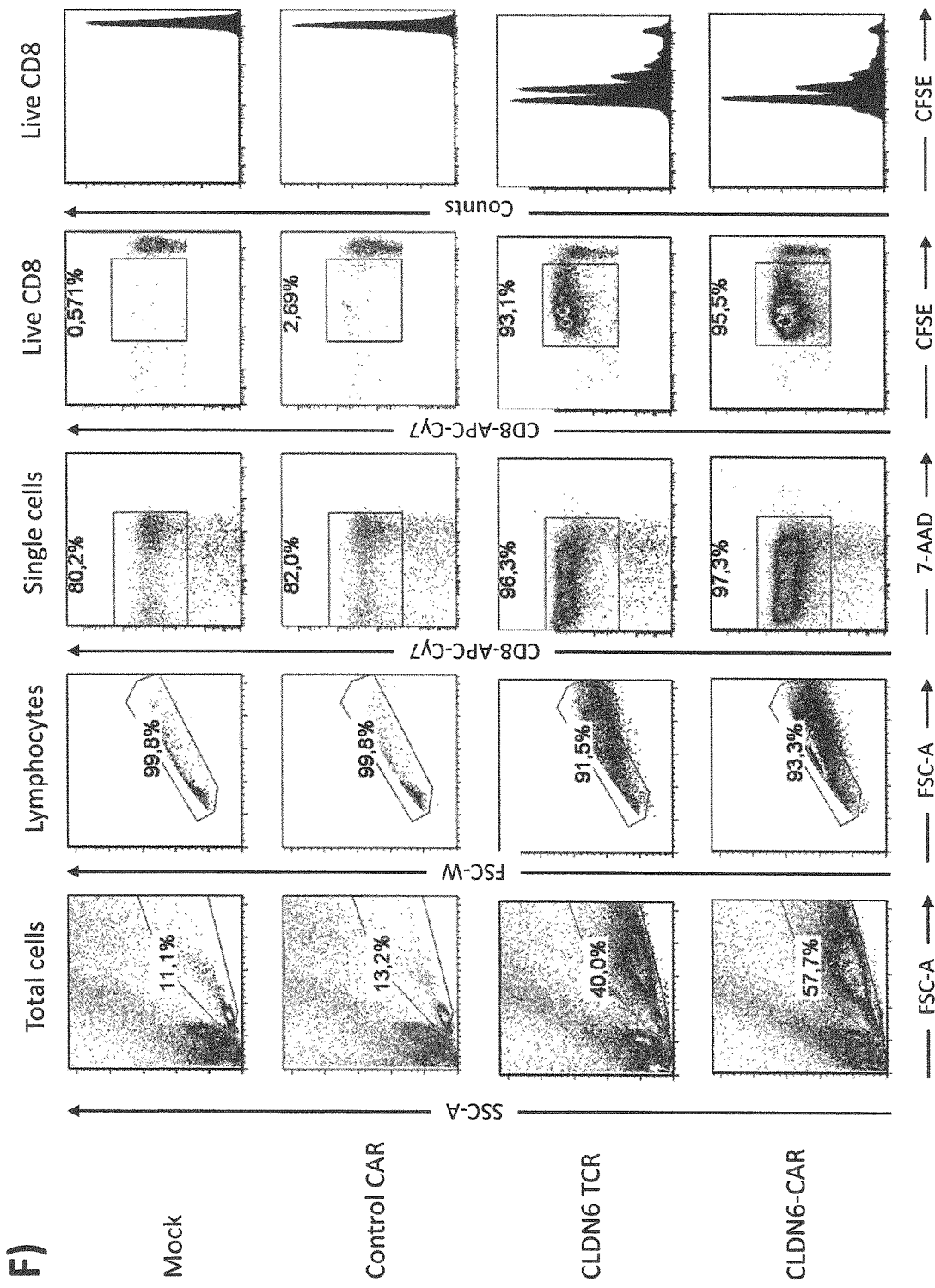

A)

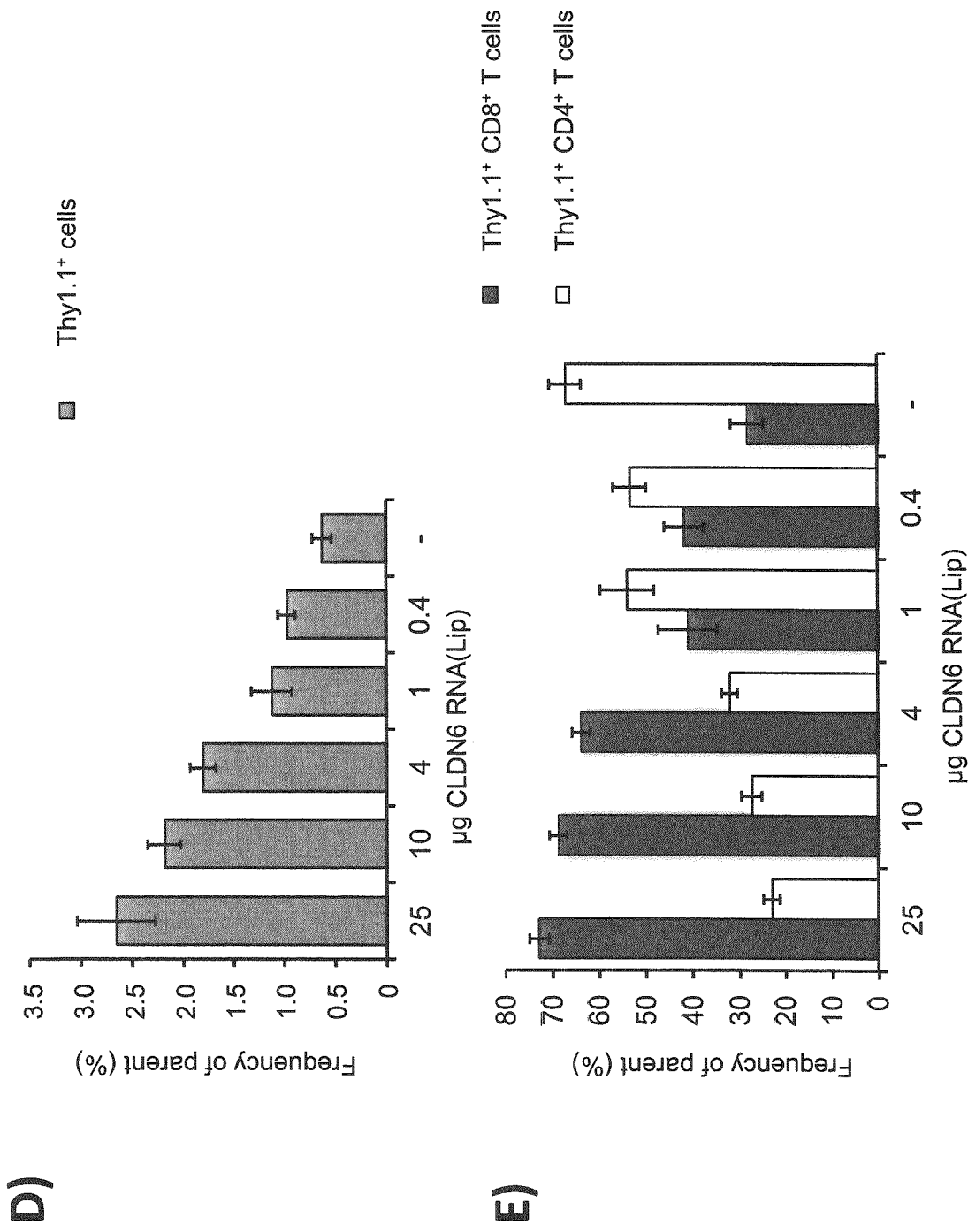

ENHANCING THE EFFECT OF CAR-ENGINEERED T CELLS BY MEANS OF NUCLEIC ACID VACCINATION

TECHNICAL FIELD OF THE INVENTION

The present invention relates to methods and means for enhancing the effect of T cells engineered to express chimeric antigen receptors (CARs).

BACKGROUND OF THE INVENTION

T cells play a central role in cell-mediated immunity in humans and animals. The recognition and binding of a particular antigen is mediated by the T cell receptors (TCRs) expressed on the surface of T cells. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell.

This diversity of TCRs is obtained by genetic rearrangement of different discontinuous segments of genes which code for the different structural regions of TCRs. TCRs are composed of one α-chain and one β-chain or of one γ-chain and one δ-chain. The TCR α/β chains are composed of an N-terminal highly polymorphic variable region involved in antigen recognition and an invariant constant region. On the genetic level, these chains are separated into several regions, a variable (V) region, a diversity (D) region (only β- and δ-chain), a joining (J) region and a constant (C) region. The human β-chain genes contain over 60 variable (V), 2 diversity (D), over 10 joining (J) segments, and 2 constant region segments (C). The human α-chain genes contain over 50 V segments, and over 60 J segments but no D segments, as well as one C segment. The murine β-chain genes contain over 30 variable (V), 2 diversity (D), over 10 joining (J) segments, and 2 constant region segments (C). The murine α-chain genes contain almost 100 V segments, 60 J segments, no D segments, but one C segment. During the differentiation of T cells, specific T cell receptor genes are created by rearranging one V, one D (only β- and δ-chain), one J and one C region gene. The diversity of the TCRs is further amplified by imprecise V-(D)-J rearrangement wherein random nucleotides are introduced and/or deleted at the recombination sites. Since the rearrangement of the TCR gene loci occurs in the genome during maturation of T cells, each mature T cell only expresses one specific α/β TCR or γ/δ TCR. MHC and antigen binding is mediated by the complementary determining regions 1, 2 and 3 (CDR1, CDR2, CDR3) of the TCR. The CDR3 of the β-chain which is most critical for antigen recognition and binding is encoded by the V-D-J junction of the rearranged TCR β-chain gene.

The TCR is a part of a complex signaling machinery, which includes the heterodimeric complex of the TCR α- and β-chains, the co-receptor CD4 or CD8 and the CD3 signal transduction modul (FIG. 1). While the CD3 chains transfer the activation signal inside the cell, the TCR α/β heterodimer is solely responsible for antigen recognition. Thus, the transfer of the TCR α/β chains offers the opportunity to redirect T cells towards any antigen of interest.

Adoptive cell transfer (ACT) based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments are lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U. S. A 99, 16168-16173). Adoptive T cell transfer was shown to have therapeutic activity against human viral infections such as CMV. While CMV infection and reactivation of endogenous latent viruses is controlled by the immune system in healthy individuals, it results in significant morbidity and mortality in immune compromised individuals such as transplant recipients or AIDS patients. Riddell and co-workers demonstrated the reconstitution of viral immunity by adoptive T cell therapy in immune suppressed patients after transfer of CD8+ CMV-specific T cell clones derived from HLA-matched CMV-seropositive transplant donors (Riddell, S. R. (1992) Science 257, 238-241). As an alternative approach polyclonal donor-derived CMV- or EBV-specific T cell populations were transferred to transplant recipients resulting in increased persistence of transferred T cells (Rooney, C. M. et al. (1998) Blood 92, 1549-1555; Peggs, K. S. et al. (2003) Lancet 362, 1375-1377). For adoptive immunotherapy of melanoma Rosenberg and co-workers established an ACT approach relying on the infusion of in vitro expanded autologous tumor-infiltrating lymphocytes (TILs) isolated from excised tumors in combination with a non-myeloablative lymphodepleting chemotherapy and high-dose IL2. A recently published clinical study resulted in an objective response rate of ~50% of treated patients suffering from metastatic melanoma (Dudley, M. E. et al. (2005) J. Clin. Oncol. 23: 2346-2357).

An alternative approach is the adoptive transfer of autologous T cells reprogrammed to express a tumor-reactive immunoreceptor of defined specificity during short-time ex vivo culture followed by reinfusion into the patient (Kershaw M. H. et al. (2013) Nature Reviews Cancer 13 (8): 525-41). This strategy makes ACT applicable to a variety of common malignancies even if tumor-reactive T cells are absent in the patient. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option. Major advantages of TCR gene transfer are the creation of therapeutic quantities of antigen-specific T cells within a few days and the possibility to introduce specificities that are not present in the endogenous TCR repertoire of the patient.

Several groups demonstrated, that TCR gene transfer is an attractive strategy to redirect antigen-specificity of primary T cells (Morgan, R. A. et al. (2003) J. Immunol. 171, 3287-3295; Cooper, L. J. et al. (2000) J. Virol. 74, 8207-8212; Fujio, K. et al. (2000) J. Immunol. 165, 528-532; Kessels, H. W. et al. (2001) Nat. Immunol. 2, 957-961; Dembic, Z. et al. (1986) Nature 320, 232-238). Feasibility of TCR gene therapy in humans was initially demonstrated in clinical trials for the treatment of malignant melanoma by Rosenberg and his group. The adoptive transfer of autologous lymphocytes retrovirally transduced with melanoma/melanocyte antigen-specific TCRs resulted in cancer regression in up to 30% of treated melanoma patients (Morgan, R. A. et al. (2006) Science 314, 126-129; Johnson, L. A. et al. (2009) Blood 114, 535-546). In the meantime clinical testing of TCR gene therapy was extended also to cancers other than melanoma targeting many different tumor antigens (Park, T. S. et al., (2011) Trends Biotechnol. 29, 550-557).

Figure 2:
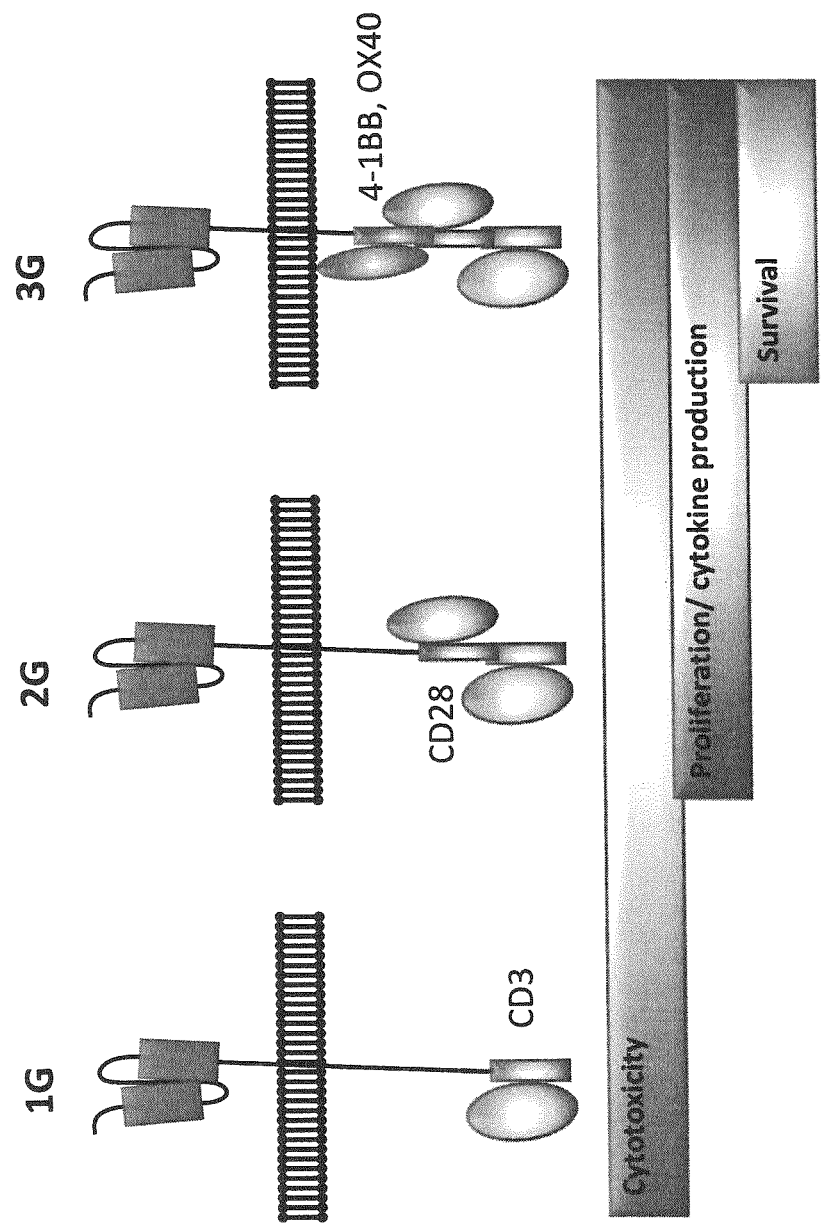

The use of genetic engineering approaches to insert antigen-targeted receptors of defined specificity into T cells has greatly extended the potential capabilities of ACT. Chimeric antigen receptors (CARs) are a type of antigen-targeted receptor composed of intracellular T cell signaling domains fused to extracellular antigen-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients. Initial CARs fused antigen-recognition domains to the CD3ξ activation chain of the T cell receptor (TCR) complex (FIG. 2). Subsequent CAR iterations have included secondary costimulatory signals in tandem with CD3ξ, including intracellular domains from CD28 or a variety of TNF receptor family molecules such as 4-1BB (CD137) and OX40 (CD134). Further, third generation receptors include two costimulatory signals in addition to CD3ξ, most commonly from CD28 and 4-1BB. Second and third generation CARs dramatically improved antitumor efficacy, in some cases inducing complete remissions in patients with advanced cancer.

It is generally thought that the number of transferred T cells is correlated with therapeutic responses. However, the number of cells which can be administered to a patient for adoptive T cell transfer is limited and the generation of a large amount of T cells for adoptive T cell transfer still remains a challenge. A substantial increase in cell persistence could be achieved when patients received a lymphodepleting preparative regimen before infusion of either TILs or receptor-engineered T cells. However, the transfer of a large amount of engineered T cells into an empty host also poses the risk of severe adverse events in case that the targeted antigen is unexpectedly expressed in a relevant normal tissue. Therefore, it would be desirable to transfer a limited amount of engineered T cells that can be expanded in the patient after they have proven to be safe. The present inventors found that it is possible to expand adoptively transferred CAR-T cells using nucleic vaccination, in particular RNA-vaccination to provide antigen for CAR-T cell stimulation. Following adoptive transfer of CAR-T cells, the T cells are subjected to an antigen-specific expansion by exposing the T cells to cells, preferably antigen presenting cells, expressing the antigen on the cell surface. Thus, it is possible to only transfer small amounts of CAR-engineered T cells into the patient and then expand the T cells in vivo by administering a nucleic acid vaccine providing an antigen.

DESCRIPTION OF INVENTION

Summary of the Invention

The present invention generally embraces the treatment of diseases by targeting cells expressing an antigen on the cell surface such as diseased cells expressing an antigen on the cell surface, in particular cancer cells expressing a tumor antigen on the cell surface. The methods provide for the selective eradication of cells that express on their surface an antigen, thereby minimizing adverse effects to normal cells not expressing the antigen. T cells genetically modified to express a chimeric antigen receptor (CAR) targeting the cells through binding to the antigen are administered. Furthermore, nucleic acid encoding the antigen or a variant thereof is administered. The nucleic acid is expressed by appropriate target cells to provide antigen for T cell stimulation, priming and/or expansion. T cells stimulated, primed and/or expanded in the patient are able to recognize cells expressing an antigen on the cell surface such as diseased cells, resulting in the eradication of diseased cells. The present approach can be considered to involve passive and active immunization. Treatment involving administration of T cells genetically modified to express a CAR can be considered as a form of passive immunization. Treatment involving administration of a nucleic acid encoding an antigen or a variant thereof, thereby stimulating a T cell-mediated immune response to a target cell population or tissue, can be considered as a form of active immunization.

In one aspect the invention relates to a method for stimulating, priming and/or expanding in vivo T cells genetically modified to express a chimeric antigen receptor (CAR) targeted to an antigen, comprising contacting the T cells with the antigen or a variant thereof in vivo. In one embodiment, the antigen or variant thereof is provided by administering a nucleic acid encoding the antigen or variant thereof. The nucleic acid is expressed by appropriate target cells to provide antigen or a variant thereof for T cell stimulation, priming and/or expansion.

In one aspect the invention relates to a method for providing an immune response to a target cell population or target tissue expressing an antigen in a mammal, the method comprising administering to the mammal T cells genetically modified to express a chimeric antigen receptor (CAR) targeted to the antigen and administering a nucleic acid encoding the antigen or a variant thereof.

In one embodiment, the immune response is a T cell-mediated immune response. In one embodiment, the immune response is an anti-tumor immune response and the target cell population or target tissue is tumor cells or tumor tissue.

In one aspect the invention relates to a method of treating a mammal having a disease, disorder or condition associated with expression or elevated expression of an antigen, the method comprising administering to the mammal T cells genetically modified to express a chimeric antigen receptor (CAR) targeted to the antigen and administering a nucleic acid encoding the antigen or a variant thereof.

In one embodiment, the disease, disorder or condition is cancer.

In one embodiment of all aspects of the invention, the antigen is a tumor antigen. In one embodiment of all aspects of the invention, the antigen is selected from the group consisting of claudins, such as claudin 6, claudin 18.2, CD19, CD20, CD22, CD33, CD123, mesothelin, CEA, c-Met, PSMA, GD-2, and NY-ESO-1. In one embodiment of all aspects of the invention, the antigen is a pathogen antigen. The pathogen may be a fungal, viral, or bacterial pathogen.

In one embodiment of all aspects of the invention, the nucleic acid encoding the antigen or variant thereof is expressed in cells of the mammal to provide the antigen or variant thereof.

In one embodiment of all aspects of the invention, expression of the antigen or variant thereof is at the cell surface.

In one embodiment of all aspects of the invention, the nucleic acid encoding the antigen or variant thereof is transiently expressed in cells of the mammal. Thus, in one embodiment, the nucleic acid encoding the antigen or variant thereof is not integrated into the genome of the cells.

In one embodiment of all aspects of the invention, the nucleic acid encoding the antigen or variant thereof is RNA, preferably in vitro transcribed RNA.

In one embodiment of all aspects of the invention, the T cells genetically modified to express a CAR and/or the nucleic acid encoding the antigen or variant thereof are administered systemically.

In one embodiment of all aspects of the invention, after systemic administration of the nucleic acid encoding the antigen or variant thereof, expression of the antigen or variant thereof in spleen occurs. In one embodiment of all aspects of the invention, after systemic administration of the nucleic acid encoding the antigen or variant thereof, expression of the antigen or variant thereof in antigen presenting cells, preferably professional antigen presenting cells occurs. In one embodiment, the antigen presenting cells are selected from the group consisting of dendritic cells, macrophages and B cells. In one embodiment of all aspects of the invention, after systemic administration of the nucleic acid encoding the antigen or variant thereof, no or essentially no expression of the antigen or variant thereof in lung and/or liver occurs. In one embodiment of all aspects of the invention, after systemic administration of the nucleic acid encoding the antigen or variant thereof, expression of the antigen or variant thereof in spleen is at least 5-fold the amount of expression in lung.

In one embodiment of all aspects of the invention, the nucleic acid encoding the antigen or variant thereof is expressed in cells of the mammal to provide the antigen or variant thereof for binding by the T cells genetically modified to express a CAR, said binding resulting in stimulation, priming and/or expansion of the T cells genetically modified to express a CAR.

In one embodiment of all aspects of the invention, the nucleic acid encoding the antigen or variant thereof is formulated in a delivery vehicle such as in particles. In one embodiment, the delivery vehicle comprises at least one lipid. In one embodiment, the at least one lipid comprises at least one cationic lipid. In one embodiment, the lipid forms a complex with and/or encapsulates the nucleic acid encoding the antigen or variant thereof. In one embodiment, the lipid is comprised in a vesicle encapsulating the nucleic acid encoding the antigen or variant thereof. In one embodiment of all aspects of the invention, the nucleic acid encoding the antigen or variant thereof is formulated in liposomes.

In one embodiment of all aspects of the invention, the method further comprises:
obtaining a sample of cells from a mammal, the sample comprising T cells or T cell progenitors, and
transfecting the cells with a nucleic acid encoding the CAR to provide T cells genetically modified to express a CAR.

In one embodiment of all aspects of the invention, the T cells genetically modified to express a CAR are stably or transiently transfected with nucleic acid encoding the CAR. Thus, the nucleic acid encoding the CAR is integrated or not integrated into the genome of the T cells.

In one embodiment of all aspects of the invention, the T cells and/or the sample of cells are from the mammal to which the T cells genetically modified to express a CAR and the nucleic acid encoding the antigen or variant thereof are administered. In one embodiment of all aspects of the invention, the T cells and/or the sample of cells are from a mammal which is different to the mammal to which the T cells genetically modified to express a CAR and the nucleic acid encoding the antigen or variant thereof are administered.

In one embodiment of all aspects of the invention, the T cells genetically modified to express a CAR are inactivated for expression of an endogenous T cell receptor and/or endogenous HLA.

In one embodiment of all aspects of the invention, the CAR comprises an antigen binding domain, a transmembrane domain, and a T cell signaling domain. In one embodiment, the antigen binding domain comprises the scFv sequence of a monoclonal antibody to the antigen.

In one aspect the invention relates to a kit comprising a nucleic acid encoding a CAR targeted to an antigen or T cells genetically modified to express a CAR targeted to an antigen and a nucleic acid encoding the antigen or a variant thereof. In one embodiment, the kit further comprises instructions for use of the kit in any of the methods of the invention.

In one embodiment of all aspects of the invention, the T cells may be autologous, allogeneic or syngeneic to the mammal. The T cells may be genetically modified in vitro to express a chimeric antigen receptor (CAR) targeted to the antigen.

In one embodiment of all aspects of the invention, an antigen is expressed in a diseased cell such as a cancer cell. In one embodiment, an antigen is expressed on the surface of a diseased cell such as a cancer cell. In one embodiment, a CAR binds to an extracellular domain or to an epitope in an extracellular domain of an antigen or a variant thereof. In one embodiment, a CAR binds to native epitopes of an antigen or a variant thereof present on the surface of living cells. In one embodiment said antigen is a claudin, in particular claudin 6 or claudin 18.2, and said CAR binds to the first extracellular loop of said claudin. In one embodiment, binding of said CAR when expressed by T cells and/or present on T cells to an antigen or a variant thereof present on cells such as antigen presenting cells results in stimulation, priming and/or expansion of said T cells. In one embodiment, binding of said CAR when expressed by T cells and/or present on T cells to an antigen present on diseased cells such as cancer cells results in cytolysis and/or apoptosis of the diseased cells, wherein said T cells preferably release cytotoxic factors, e.g. performs and granzymes.

In one embodiment of all aspects of the invention, a CAR comprises an antigen binding domain. In one embodiment, the antigen binding domain is comprised by an exodomain of a CAR. In one embodiment, the antigen binding domain comprises a single-chain variable fragment (scFv) of an antibody to the antigen. In one embodiment, the antigen binding domain comprises a variable region of a heavy chain of an immunoglobulin (VH) with a specificity for the antigen (VH(antigen)) and a variable region of a light chain of an immunoglobulin (VL) with a specificity for the antigen (VL(antigen)). In one embodiment, said heavy chain variable region (VH) and the corresponding light chain variable region (VL) are connected via a peptide linker, preferably a peptide linker comprising the amino acid sequence (GGGGS)3.

In one embodiment of all aspects of the invention, a CAR comprises a transmembrane domain. In one embodiment, the transmembrane domain is a hydrophobic alpha helix that spans the membrane. In one embodiment, the transmembrane domain comprises the CD28 transmembrane domain or a fragment thereof.

In one embodiment of all aspects of the invention, a CAR comprises a T cell signaling domain. In one embodiment, the T cell signaling domain is located intracellularly. In one embodiment, the T cell signaling domain comprises CD3-zeta, preferably the endodomain of CD3-zeta, optionally in combination with CD28. In one embodiment, the T cell signaling domain comprises the sequence according to SEQ ID NO: 8 or a fragment thereof, or a variant of said sequence or fragment.

In one embodiment of all aspects of the invention, a CAR comprises a signal peptide which directs the nascent protein into the endoplasmic reticulum. In one embodiment, the signal peptide precedes the antigen binding domain. In one embodiment, the signal peptide comprises the sequence according to SEQ ID NO: 5 or a fragment thereof, or a variant of said sequence or fragment.

In one embodiment of all aspects of the invention, a CAR comprises a spacer region which links the antigen binding domain to the transmembrane domain. In one embodiment, the spacer region allows the antigen binding domain to orient in different directions to facilitate antigen recognition. In one embodiment, the spacer region comprises the hinge region from IgG1. In one embodiment, the spacer region comprises the sequence according to SEQ ID NO: 6 or a fragment thereof, or a variant of said sequence or fragment.

In one embodiment of all aspects of the invention, a CAR comprises the structure:

NH2—signal peptide—antigen binding domain—spacer region—transmembrane domain—T cell signaling domain—COOH.

In one embodiment of all aspects of the invention, a CAR is preferably specific for the antigen to which it is targeted, in particular when present on the surface of a cell such as a diseased cell or an antigen-presenting cell.

In one embodiment of all aspects of the invention, a CAR may be expressed by and/or present on the surface of a T cell, preferably a cytotoxic T cell. In one embodiment, the T cell is reactive with the antigen to which the CAR is targeted.

In one embodiment of all aspects of the invention, the T cells genetically modified to express a CAR and/or the nucleic acid encoding an antigen or a variant thereof either together or separate from each other may be administered in a pharmaceutical composition which may comprise a pharmaceutically acceptable carrier and may optionally comprise one or more adjuvants, stabilizers etc. In one embodiment, the pharmaceutical composition is for use in treating or preventing a disease involving an antigen such as a cancer disease such as those described herein.

In a further aspect, the invention provides the agents and compositions described herein for use in the methods described herein.

In one aspect, the invention relates to T cells genetically modified to express a chimeric antigen receptor (CAR) targeted to an antigen for use in the methods of the invention.

In one aspect, the invention relates to a nucleic acid encoding an antigen or a variant thereof for use in the methods of the invention.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "immune response" refers to an integrated bodily response to an antigen and preferably refers to a cellular immune response or a cellular as well as a humoral immune response. The immune response may be protective/preventive/prophylactic and/or therapeutic.

"Providing an immune response" may mean that there was no immune response against a particular target antigen, target cell and/or target tissue before providing an immune response, but it may also mean that there was a certain level of immune response against a particular target antigen, target cell and/or target tissue before providing an immune response and after providing an immune response said immune response is enhanced. Thus, "providing an immune response" includes "inducing an immune response" and "enhancing an immune response". Preferably, after providing an immune response in a subject, said subject is protected from developing a disease such as a cancer disease or the disease condition is ameliorated by providing an immune response. For example, an immune response against a tumor antigen may be provided in a patient having a cancer disease or in a subject being at risk of developing a cancer disease. Providing an immune response in this case may mean that the disease condition of the subject is ameliorated, that the subject does not develop metastases, or that the subject being at risk of developing a cancer disease does not develop a cancer disease.

"Cell-mediated immunity" or "cellular immunity", or similar terms are meant to include a cellular response directed to cells characterized by expression of an antigen, in particular characterized by presentation of an antigen with class I or class II MHC. The cellular response relates to cells called T cells or T-lymphocytes which act as either 'helpers' or 'killers'. The helper T cells (also termed CD4$^+$ T cells) play a central role by regulating the immune response and the killer cells (also termed cytotoxic T cells, cytolytic T cells, CD8$^+$ T cells or CTLs) kill diseased cells such as cancer cells, preventing the production of more diseased cells.

The term "antigen" relates to an agent comprising an epitope against which an immune response is to be generated and/or is directed. Preferably, an antigen in the context of the present invention is a molecule which, optionally after processing, induces an immune reaction, which is preferably specific for the antigen or cells expressing the antigen, preferably on the cell surface. The term "antigen" includes in particular proteins and peptides. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof.

The term "pathogen" relates to pathogenic microorganisms and comprises viruses, bacteria, fungi, unicellular organisms, and parasites. Examples for pathogenic viruses are human immunodeficiency virus (HIV), cytomegalovirus (CMV), herpes virus (HSV), hepatitis A-virus (HAV), HBV, HCV, papilloma virus, and human T-lymphotrophic virus (HTLV). Unicellular organisms comprise plasmodia, trypanosomes, amoeba, etc.

In a preferred embodiment, an antigen is a disease-associated antigen. The term "disease-associated antigen" refers to all antigens that are of pathological significance. In one particularly preferred embodiment, a disease-associated antigen is present in diseased cells, tissues and/or organs while it is not present or present in a reduced amount in healthy cells, tissues and/or organs and, thus, can be used for targeting diseased cells, tissues and/or organs, e.g. by T cells carrying a CAR targeted to the antigen. In one embodiment, a disease-associated antigen is present on the surface of a diseased cell.

In a preferred embodiment, an antigen is a tumor antigen or tumor-associated antigen, i.e., a constituent of cancer cells which may be derived from the cytoplasm, the cell surface and the cell nucleus, in particular those antigens which are produced, preferably in large quantity, as surface antigens on cancer cells.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE- A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

The term "CLDN" as used herein means claudin and includes CLDN6 and CLDN18.2. Preferably, a claudin is a human claudin. Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family are expressed in tumors of various origins, and are particularly suited as target structures in connection with antibody-mediated cancer immunotherapy due to their selective expression (no expression in a toxicity relevant normal tissue) and localization to the plasma membrane.

CLDN6 and CLDN18.2 have been identified as differentially expressed in tumor tissues, with the only normal tissues expressing CLDN18.2 being stomach and the only normal tissue expressing CLDN6 being placenta.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 1. The second extracellular loop of CLDN18.2 preferably comprises amino acids 140 to 180 of the amino acid sequence shown in SEQ ID NO: 1. Said first and second extracellular loops preferably form the extracellular portion of CLDN18.2.

The term "CLDN6" preferably relates to human CLDN6, and, in particular, to a protein comprising, preferably consisting of the amino acid sequence of SEQ ID NO: 2 or SEQ ID NO: 3 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 2 or the amino acid sequence shown in SEQ ID NO: 3. The second extracellular loop of CLDN6 preferably comprises amino acids 138 to 160, preferably amino acids 141 to 159, more preferably amino acids 145 to 157 of the amino acid sequence shown in SEQ ID NO: 2 or the amino acid sequence shown in SEQ ID NO: 3. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

An antigen or variant thereof encoded by the nucleic acid to be administered according to the invention, i.e. a vaccine antigen, should result in stimulation, priming and/or expansion of CAR-engineered T cells. Said stimulated, primed and/or expanded T cells should be directed against a target antigen, in particular a target antigen expressed on diseased cells, tissues and/or organs, i.e. a disease-associated antigen. Thus, a vaccine antigen may correspond to the disease-associated antigen, or it may be a variant thereof. In one embodiment, such variant is immunologically equivalent to the disease-associated antigen. In the context of the present invention, the term "variant of an antigen" means an agent which results in stimulation, priming and/or expansion of CAR-engineered T cells which stimulated, primed and/or expanded T cells target the antigen, i.e. a disease-associated antigen, in particular when expressed on diseased cells, tissues and/or organs. Thus, the vaccine antigen encoded by the nucleic acid to be administered according to the invention may be identical to the disease-associated antigen, may comprise the disease-associated antigen or a portion thereof or may comprise an antigen which is homologous to the disease-associated antigen or a portion thereof. If the vaccine antigen encoded by the nucleic acid to be administered according to the invention comprises a portion of the disease-associated antigen or a portion of an antigen which is homologous to the disease-associated antigen said portion may comprise the epitope of the disease-associated antigen to which the CAR of the CAR-engineered T cells is targeted. Thus, according to the invention, an antigen encoded by the nucleic acid to be administered may comprise an immunogenic fragment of a disease-associated antigen such as a peptide fragment of a disease-associated antigen. An "immunogenic fragment of an antigen" according to the invention preferably relates to a portion or fragment of an antigen which is capable of stimulating, priming and/or expanding T cells carrying a CAR binding to the antigen or cells expressing the antigen. It is preferred that the vaccine antigen (similar to the disease-associated antigen) can be expressed on the surface of a cell such as an antigen-presenting cell so as to provide the relevant epitope for binding by the CAR on T cells. The vaccine antigen encoded by the nucleic acid to be administered according to the invention may be a recombinant antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present invention, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject such as T cells carrying a CAR binding to the reference amino acid sequence or cells expressing the reference amino acid sequence induces an immune reaction having a specificity of reacting with the reference amino acid sequence. Thus, a molecule which is immunologically equivalent to an antigen exhibits the same or essentially the same properties and/or exerts the same or essentially the same effects regarding the stimulation, priming and/or expansion of CAR-engineered T cells as the antigen to which the CAR-engineered T cells are targeted.

According to the invention, the antigen or variant thereof should be recognizable by a CAR. Preferably, the antigen or variant thereof if recognized by a CAR is able to induce in the presence of appropriate co-stimulatory signals, stimulation, priming and/or expansion of the T cell carrying the CAR recognizing the antigen or variant thereof. In the context of the embodiments of the present invention, the antigen or variant thereof is preferably present on the surface of a cell, preferably an antigen presenting cell. Recognition of the antigen on the surface of a diseased cell may result in an immune reaction against the antigen (or cell expressing the antigen).

According to the various aspects of the invention, the aim is preferably to provide an immune response against cancer cells expressing a tumor antigen such as CLDN6 or CLDN18.26 and to treat a cancer disease involving cells expressing a tumor antigen such as CLDN6 or CLDN18.2. Preferably the invention involves the administration of CAR-engineered T cells targeted against cancer cells expressing a tumor antigen such as CLDN6 or CLDN18.2.

According to the invention, the term "tumor antigen positive cancer" or similar terms means a cancer involving cancer cells expressing a tumor antigen, preferably on the surface of said cancer cells. Cancer cells expressing a tumor antigen on the surface can be targeted by immunoreactive cells carrying a CAR targeted to the tumor antigen.

"Cell surface" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells. In one embodiment, an antigen expressed on the surface of cells is an integral membrane protein having an extracellular portion recognized by a CAR.

The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The terms "portion" or "part" are used interchangeably herein and refer to a continuous or discontinuous element of a structure such as an amino acid sequence. The term "fragment" refers to a continuous element of a structure such as an amino acid sequence. A portion, part or fragment of a structure preferably comprises one or more functional properties, e.g. antigenic, immunologic and/or binding properties, of said structure. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence According to the invention, an antigen is not (substantially) expressed in a cell if the level of expression is below the detection limit and/or if the level of expression is too low to allow binding by antigen-specific antibodies added to the cell. According to the invention, an antigen is expressed in a cell if the level of expression is above the detection limit and/or if the level of expression is high enough to allow binding by antigen-specific antibodies added to the cell. Preferably, an antigen expressed in a cell is expressed or exposed, i.e. is present, on the surface of said cell and, thus, available for binding by antigen-specific molecules such as antibodies or CAR molecules added to the cell.

"Target cell" shall mean a cell which is a target for an immune response such as a cellular immune response. Target cells include any undesirable cell such as a cancer cell. In preferred embodiments, the target cell is a cell expressing a target antigen which preferably is present on the cell surface.

The term "epitope" refers to an antigenic determinant in a molecule such as an antigen, i.e., to a part in or fragment of the molecule that is recognized, i.e. bound, by the immune system, for example, that is recognized by an antibody or CAR. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably an epitope is capable of eliciting an immune response against the antigen or a cell expressing the antigen. Preferably, the term relates to an immunogenic portion of an antigen. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells. According to the invention, the term "antigen-presenting cell" includes professional antigen-presenting cells and non-professional antigen-presenting cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

The term "immunogenicity" relates to the relative efficiency of an antigen to induce an immune reaction.

The term "immune effector functions" in the context of the present invention includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the release of cytokines and/or the activation of CD8$^+$ lymphocytes (CTLs) and/or B-cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immunoreactive cell" or "immune effector cell" in the context of the present invention relates to a cell which exerts effector functions during an immune reaction. An "immunoreactive cell" preferably is capable of binding an antigen such as an antigen expressed on the surface of a cell and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably CD4$^+$ and/or CD8$^+$ T cells. According to the invention, the term "immunoreactive cell" also includes a cell which can mature into an immune cell (such as T cell, in particular T helper cell, or cytolytic T cell) with suitable stimulation. Immunoreactive cells comprise CD34$^+$ hematopoietic stem cells, immature and mature T cells and immature and mature B cells. The differentiation of T cell precursors into a cytolytic T cell, when exposed to an antigen, is similar to clonal selection of the immune system.

Preferably, an "immunoreactive cell" recognizes an antigen with some degree of specificity, in particular if present on the surface of antigen presenting cells or diseased cells such as cancer cells. Preferably, said recognition enables the cell that recognizes an antigen to be responsive or reactive. If the cell is a helper T cell (CD4+ T cell) such responsiveness or reactivity may involve the release of cytokines and/or the activation of CD8+ lymphocytes (CTLs) and/or B-cells. If the cell is a CTL such responsiveness or reactivity may involve the elimination of cells, i.e., cells characterized by expression of an antigen, for example, via apoptosis or perform-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen and are responsive or reactive are also termed "antigen-responsive CTL" herein.

A "lymphoid cell" is a cell which, optionally after suitable modification, e.g. after transfer of a T cell receptor or CAR, is capable of producing an immune response such as a cellular immune response, or a precursor cell of such cell, and includes lymphocytes, preferably T lymphocytes, lymphoblasts, and plasma cells. A lymphoid cell may be an immunoreactive cell as described herein. A preferred lymphoid cell is a T cell which can be modified to express a T cell receptor or CAR on the cell surface. In one embodiment, the lymphoid cell lacks endogenous expression of a T cell receptor.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development they become double-positive thymocytes (CD4+CD8+), and finally mature to single-positive (CD4+CD8− or CD4−CD8+) thymocytes that are then released from the thymus to peripheral tissues.

T cells may generally be prepared in vitro or ex vivo, using standard procedures. For example, T cells may be isolated from bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A sample comprising T cells may, for example, be peripheral blood mononuclear cells (PBMC).

The T cells to be used according to the invention may express an endogenous T cell receptor or may lack expression of an endogenous T cell receptor.

Nucleic acids such as RNA encoding a CAR may be introduced into T cells or other cells with lytic potential, in particular lymphoid cells.

The term "CAR targeted to an antigen" relates to a CAR which when present on an immunoreactive cell such as a T cell recognizes the antigen such as on the surface of antigen presenting cells or diseased cells such as cancer cells, such that the immunoreactive cell is stimulated, primed and/or expanded or exerts effector functions of immunoreactive cells as described above.

The term "antigen-specific T cell" or similar terms relate to a T cell which, in particular when provided with a CAR, recognizes the antigen to which the CAR is targeted such as on the surface of antigen presenting cells or diseased cells such as cancer cells and preferably exerts effector functions of T cells as described above. T cells and other lymphoid cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

According to the invention the term "chimeric antigen receptor (CAR)" is synonymous with the terms "chimeric T cell receptor" and "artificial T cell receptor".

These terms relate to engineered receptors, which confer an arbitrary specificity such as the specificity of a monoclonal antibody onto an immune effector cell such as a T cell. In this way, a large number of cancer-specific T cells can be generated for adoptive cell transfer. Thus, a CAR may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said CAR is expressed on the surface of the cells. For the purpose of the present invention T cells comprising a CAR are comprised by the term "T cell" as used herein.

According to the invention, the term "CAR" (or "chimeric antigen receptor") relates to an artificial receptor comprising a single molecule or a complex of molecules which recognizes, i.e. binds to, a target structure (e.g. an antigen) on a target cell such as a cancer cell (e.g. by binding of an antigen binding domain to an antigen expressed on the surface of the target cell) and may confer specificity onto an immune effector cell such as a T cell expressing said CAR on the cell surface. Preferably, recognition of the target structure by a CAR results in activation of an immune effector cell expressing said CAR. A CAR may comprise one or more protein units said protein units comprising one or more domains as described herein. The term "CAR" does not include T cell receptors.

In one embodiment, a single-chain variable fragment (scFv) derived from a monoclonal antibody is fused to CD3-zeta transmembrane and endodomain. Such molecules result in the transmission of a zeta signal in response to recognition by the saw of its antigen target on a target cell and killing of the target cell that expresses the target antigen. Antigen recognition domains which also may be used include among others T cell receptor (TCR) alpha and beta single chains. In fact almost anything that binds a given target with high affinity can be used as an antigen recognition domain.

Following antigen recognition, receptors cluster and a signal is transmitted to the cell. In this respect, a "T cell signaling domain" is a domain, preferably an endodomain, which transmits an activation signal to the T cell after antigen is bound. The most commonly used endodomain component is CD3-zeta.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered (genetically modified) to express CARs specifically directed towards antigens on the patient's tumor cells, then infused back into the patient.

According to the invention a CAR may replace the function of a T cell receptor as described above and, in particular, may confer reactivity such as cytolytic activity to a cell such as a T cell as described above. However, in contrast to the binding of the T cell receptor to an antigen peptide-MHC complex as described above, a CAR may bind to an antigen, in particular when expressed on the cell surface.

The T cell surface glycoprotein CD3-zeta chain is a protein that in humans is encoded by the CD247 gene. CD3-zeta together with T cell receptor alpha/beta and gamma/delta heterodimers and CD3-gamma, -delta, and -epsilon, forms the T cell receptor-CD3 complex. The zeta chain plays an important role in coupling antigen recognition to several intracellular signal-transduction pathways. The term "CD3-zeta" preferably relates to human CD3-zeta, and, in particular, to a protein comprising, preferably consisting of the amino acid sequence of SEQ ID NO: 8 of the sequence listing or a variant of said amino acid sequence.

CD28 (Cluster of Differentiation 28) is one of the molecules expressed on T cells that provide co-stimulatory signals, which are required for T cell activation. CD28 is the receptor for CD80 (B7.1) and CD86 (B7.2). Stimulation through CD28 in addition to the T cell receptor (TCR) can provide a potent co-stimulatory signal to T cells for the production of various interleukins (IL-6 in particular). The term "CD28" preferably relates to human CD28, and, in particular, to a protein comprising, preferably consisting of the amino acid sequence of SEQ ID NO: 7 of the sequence listing or a variant of said amino acid sequence.

According to the invention, CARs may generally comprise three domains.

The first domain is the binding domain which recognizes and binds antigen.

The second domain is the co-stimulation domain. The co-stimulation domain serves to enhance the proliferation and survival of the cytotoxic lymphocytes upon binding of the CAR to a targeted moiety. The identity of the co-stimulation domain is limited only in that it has the ability to enhance cellular proliferation and survival upon binding of the targeted moiety by the CAR. Suitable co-stimulation domains include CD28, CD137 (4-1BB), a member of the tumor necrosis factor (TNF) receptor family, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+ CD137 (4-1BB) and CD28+CD134 (OX40).

The third domain is the activation signaling domain (or T cell signaling domain) The activation signaling domain serves to activate cytotoxic lymphocytes upon binding of the CAR to antigen. The identity of the activation signaling domain is limited only in that it has the ability to induce activation of the selected cytotoxic lymphocyte upon binding of the antigen by the CAR. Suitable activation signaling domains include the T cell CD3 [zeta] chain and Fc receptor [gamma]. The skilled artisan will understand that sequence variants of these noted activation signaling domains can be used without adversely impacting the invention, where the variants have the same or similar activity as the domain on which they are modeled. Such variants will have at least about 80% sequence identity to the amino acid sequence of the domain from which they are derived.

The CARs of the present invention may comprise the three domains, together in the form of a fusion protein. Such fusion proteins will generally comprise a binding domain, one or more co-stimulation domains, and an activation signaling domain, linked in a N-terminal to C-terminal direction. However, the CARs of the present invention are not limited to this arrangement and other arrangements are acceptable and include a binding domain, an activation signaling domain, and one or more co-stimulation domains. It will be understood that because the binding domain must be free to bind antigen, the placement of the binding domain in the fusion protein will generally be such that display of the region on the exterior of the cell is achieved. In the same manner, because the co-stimulation and activation signaling domains serve to induce activity and proliferation of the cytotoxic lymphocytes, the fusion protein will generally display these two domains in the interior of the cell. The CARs may include additional elements, such as a signal peptide to ensure proper export of the fusion protein to the cells surface, a transmembrane domain to ensure the fusion protein is maintained as an integral membrane protein, and a hinge domain (or spacer region) that imparts flexibility to the binding domain and allows strong binding to antigen.

The cells used in connection with the CAR system of the present invention are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cytotoxic lymphocytes will preferably be autologous cells, although heterologous cells or allogenic cells can be used.

A variety of methods may be used to introduce CAR constructs into T cells including non-viral-based DNA transfection, transposon-based systems and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

According to the invention, the term "antigen binding domain" includes and preferably relates to the antigen-binding portion of an antibody to the antigen, i.e. an antibody which is directed against the antigen and is preferably specific for the antigen.

The term "binding domain" characterizes in connection with the present invention a structure, e.g. of an antibody, which binds to/interacts with a given target structure/antigen/epitope. Thus, the binding domain according to the invention designates an "antigen-interaction-site".

Antibodies and derivatives of antibodies are useful for providing binding domains such as antibody fragments, in particular for providing VL and VH regions.

A binding domain for an antigen which may be present within a CAR has the ability of binding to (targeting) an antigen, i.e. the ability of binding to (targeting) an epitope present in an antigen, preferably an epitope located within the extracellular domain of an antigen. Preferably, a binding domain for an antigen is specific for the antigen. Preferably, a binding domain for an antigen binds to the antigen expressed on the cell surface. In particular preferred embodiments, a binding domain for an antigen binds to native epitopes of an antigen present on the surface of living cells.

All antibodies and derivatives of antibodies such as antibody fragments as described herein for the purposes of the invention are encompassed by the term "antibody".

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

The ability of antibodies and other binding agents to bind an antigen can be determined using standard binding assays (e.g., ELISA, Western Blot, Immunofluorescence and flow cytometric analysis).

The term "binding" according to the invention preferably relates to a specific binding.

According to the present invention, an agent such as a CAR is capable of binding to (targeting) a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to (targeting) a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent is specific for a predetermined target if it is capable of binding to said predetermined target while it is not (substantially) capable of binding to other targets, i.e. has no significant affinity for other targets and does not significantly bind to other targets in standard assays. Preferably, an agent is specific for a predetermined target if the affinity for and the binding to such other targets does not significantly exceed the affinity for or binding to proteins which are unrelated to a predetermined target such as bovine serum albumin (BSA), casein or human serum albumin (HSA). Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Preferably, according to the invention, a nucleic acid such as RNA that codes for an antigen or a variant thereof is introduced into a mammal. The nucleic acid is taken up into the mammal's antigen-presenting cells (monocytes, macrophages, dendritic cells or other cells). An antigenic translation product of the nucleic acid is formed and the product is displayed on the surface of the cells for recognition by CAR-engineered T cells directed to the antigen.

Alternatively, the present invention envisions embodiments wherein a nucleic acid expressing an antigen recited herein is introduced into antigen-presenting cells ex vivo, e.g. antigen-presenting cells taken from a patient, and the antigen-presenting cells, optionally clonally propagated ex vivo, are transplanted back into the same patient. Transfected cells may be reintroduced into the patient using any means known in the art, preferably in sterile form by intravenous, intracavitary, intraperitoneal or intratumor administration.

The methods of the invention may involve an antigen presenting cell for expressing the nucleic acid encoding the antigen or a variant thereof. To this end, the methods of the invention may involve introduction of nucleic acids encoding antigens into antigen presenting cells such as dendritic cells. For transfection of antigen presenting cells such as dendritic cells a pharmaceutical composition comprising nucleic acid encoding the antigen may be used. A delivery vehicle that targets the nucleic acid to a dendritic or other antigen presenting cell may be administered to a patient, resulting in transfection that occurs in vivo.

According to the invention it is preferred to use formulations of the nucleic acid encoding an antigen or a variant thereof which deliver the nucleic acid with high selectivity to antigen presenting cells such as dendritc cells (DCs) in the spleen after systemic administration. For example, nanoparticulate RNA formulations with defined particle size wherein the net charge of the particles is close to zero or negative, such as electro-neutral or negatively charged lipoplexes from RNA and liposomes, e.g. lipoplexes comprising DOTMA and DOPE or DOTMA and Cholesterol, lead to substantial RNA expression in spleen DCs after systemic administration. A strong expression in the target cells (spleen) was determined while the expression in other organs was low.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm.

As used herein, the term "nanoparticulate formulation" or similar terms refer to any substance that contains at least one nanoparticle. In some embodiments, a nanoparticulate composition is a uniform collection of nanoparticles. In some embodiments, nanoparticulate compositions are dispersions or emulsions. In general, a dispersion or emulsion is formed when at least two immiscible materials are combined.

The term, "lipoplex" or "nucleic acid lipoplex", in particular "RNA lipoplex", refers to a complex of lipids and nucleic acids, in particular RNA. Lipoplexes are formed spontaneously when cationic liposomes, which often also include a neutral "helper" lipid, are mixed with nucleic acids.

If the present invention refers to a charge such as a positive charge, negative charge or neutral charge or a cationic compound, negative compound or neutral compound this generally means that the charge mentioned is present at a selected pH, such as a physiological pH. For example, the term "cationic lipid" means a lipid having a net positive charge at a selected pH, such as a physiological pH. The term "neutral lipid" means a lipid having no net positive or negative charge and can be present in the form of a non-charge or a neutral amphoteric ion at a selected pH, such as a physiological pH. By "physiological pH" herein is meant a pH of about 7.5.

The nanoparticulate carriers such as lipid carriers contemplated for use in the present invention include any substances or vehicles with which nucleic acid such as RNA can be associated, e.g. by forming complexes with the nucleic acid or forming vesicles in which the nucleic acid is enclosed or encapsulated. This may result in increased stability of the nucleic acid compared to naked nucleic acid. In particular, stability of the nucleic acid in blood may be increased.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate nucleic acid preparations for use in the present invention can be obtained by various protocols and from various nucleic acid complexing compounds. Lipids, polymers, oligomers, or amphipiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine. In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate nucleic acid formulations of the present invention.

For formation of nucleic acid lipoplexes from nucleic acid and liposomes, any suitable method of forming liposomes can be used so long as it provides the envisaged nucleic acid lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the nucleic acid-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene, glycol-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of nucleic acid to the lipid carrier can occur, for example, by the nucleic acid filling interstitial spaces of the carrier, such that the carrier physically entraps the nucleic acid, or by covalent, ionic, or hydrogen bonding, or by means of adsorption by non-specific bonds. Whatever the mode of association, the nucleic acid must retain its therapeutic, i.e. antigen-encoding, properties.

In particular embodiments, the nucleic acid encoding an antigen or a variant thereof is administered before, simultaneously with and/or after administration of CAR-engineered T cells. Preferably the nucleic acid encoding an antigen or a variant thereof is administered following administration of CAR-engineered T cells.

The CAR-engineered T cells and the nucleic acid encoding an antigen or a variant thereof can be present in a common composition, i.e. mixed together. Moreover, embodiments are also envisaged according to the invention in which the CAR-engineered T cells and the nucleic acid encoding an antigen or a variant thereof are present together, but not in the same composition. Said embodiments relate in particular to kits with at least two containers, where one container contains a composition comprising the CAR-engineered T cells, and another container contains a composition comprising the nucleic acid encoding an antigen or a variant thereof.

According to the invention, the nucleic acid encoding an antigen or a variant thereof in one embodiment is RNA, preferably mRNA. The RNA is preferably obtained by in-vitro transcription.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a nucleic acid is preferably an isolated nucleic acid.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the agents described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of an mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "nucleic acid encoding" means that nucleic acid, if present in the appropriate environment, preferably within a cell, can be expressed to produce a protein or peptide it encodes.

The nucleic acids described herein may be recombinant and/or isolated molecules.

An "isolated molecule" as used herein, is intended to refer to a molecule which is substantially free of other molecules such as other cellular material.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, any technique useful for introducing, i.e. transferring or transfecting, nucleic acids into cells may be used. Preferably, RNA is transfected into cells by standard techniques. Such techniques include electroporation, lipofection and microinjection. In one particularly preferred embodiment of the present invention, RNA is introduced into cells by electroporation. Electroporation or electropermeabilization relates to a significant increase in the electrical conductivity and permeability of the cell plasma membrane caused by an externally applied electrical field. It is usually used in molecular biology as a way of introducing some substance into a cell. According to the invention it is preferred that introduction of nucleic acid encoding a protein or peptide into cells results in expression of said protein or peptide.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of a peptide to its target.

It will be appreciated by those skilled in the art that in particular the sequences of the CDR sequences, hypervariable and variable regions can be modified without losing the ability to bind to a target. For example, CDR regions will be either identical or highly homologous to the regions of parental antibodies. By "highly homologous" it is contemplated that from 1 to 5, preferably from 1 to 4, such as 1 to 3 or 1 or 2 substitutions may be made in the CDRs.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains.

Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

According to the invention, a variant, fragment, part or portion of an amino acid sequence, peptide or protein preferably has a functional property of the amino acid sequence, peptide or protein, respectively, from which it has been derived, i.e. it is functionally equivalent. In one embodiment, a variant, fragment, part or portion of an amino acid sequence, peptide or protein is immunologically equivalent to the amino acid sequence, peptide or protein, respectively, from which it has been derived. In one embodiment, the functional property is an immunological property.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus,* and *Pseudomonas,* and gram-positive bacterial strains such as strains of *Bacillus, Streptomyces, Staphylococcus,* and *Lactococcus.* Suitable fungal cell include cells from species of *Trichoderma, Neurospora,* and *Aspergillus.* Suitable yeast cells include cells from species of *Saccharomyces* (Tor example *Saccharomyces cerevisiae*), *Schizosaccharomyces* (for example Schizo *saccharomyces pombe*), *Pichia* (for example *Pichia pastoris* and *Pichia methanolicd*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

A cell which comprises a nucleic acid molecule preferably express the peptide or protein encoded by the nucleic acid.

The term "priming" refers to a process wherein a T cell has its first contact with its specific antigen and causes differentiation into effector T cells.

The term "clonal expansion" or "expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

"Reduce" or "inhibit" as used herein means the ability to cause an overall decrease, preferably of 5% or greater, 10% or greater, 20% or greater, more preferably of 50% or greater, and most preferably of 75% or greater, in the level.

The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to treat a subject with a disease, e.g., a disease characterized by the presence of diseased cells expressing an antigen. Particularly preferred diseases are cancer diseases.

The agents, compositions and methods described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes infectious diseases and cancer diseases, in particular those forms of cancer described herein. Any reference herein to cancer or particular forms of cancer also includes cancer metastasis thereof.

A disease to be treated according to the invention is preferably a disease involving an antigen. "Disease involving an antigen", "disease associated with expression or elevated expression of an antigen" or similar expressions means according to the invention that the antigen is expressed in cells of a diseased tissue or organ. Expression in cells of a diseased tissue or organ may be increased compared to the state in a healthy tissue or organ. In one embodiment, expression is only found in a diseased tissue, while expression in a healthy tissue is repressed. According to the invention, diseases involving an antigen include infectious diseases and cancer diseases, wherein the disease-associated antigen is preferably an antigen of the infectious agent and a tumor antigen, respectively. Preferably a disease involving an antigen preferably is a disease involving cells expressing an antigen, preferably on the cell surface.

The term "healthy" or "normal" refer to non-pathological conditions, and preferably means non-infected or non-cancerous.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen and a cancer cell expresses a tumor antigen.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of an agent or composition of the invention, preferably protects the recipient from the development of a disease. A therapeutic administration of an immunotherapy, for example, a therapeutic administration of an agent or composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein preferably function to remove antigen-expressing cells from a patient. Such removal may take place as a result of enhancing or inducing an immune response in a patient specific for antigen or a cell expressing antigen.

Active immunotherapy is a form of immunotherapy, in which treatment relies on the in vivo stimulation of the endogenous host immune system to react against diseased cells with the administration of immune response-modifying agents (such as nucleic acids encoding an antigen).

Passive immunotherapy is a form of immunotherapy, in which treatment involves the delivery of agents with established tumor-immune reactivity (such as effector cells) that can directly or indirectly mediate antitumor effects and does not necessarily depend on an intact host immune system. Examples of effector cells include T lymphocytes (such as CD8+ cytotoxic T lymphocytes and CD4+T-helper lymphocytes), and antigen-presenting cells (such as dendritic cells and macrophages). Artificial T cell receptors specific for an antigen may be transferred into effector cells for adoptive immunotherapy.

The term "immunization" or "vaccination" describes the process of treating a subject with the purpose of inducing an immune response for therapeutic or prophylactic reasons.

The term "in vivo" relates to the situation in a subject.

The compounds and agents described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by expression of an antigen.

For example, in one embodiment, agents described herein can be used to treat a patient with a cancer disease, e.g., a cancer disease such as described herein characterized by the presence of cancer cells expressing an antigen.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFNα, IFNγ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

Administration may also be carried out, for example, orally, intraperitonealy or intramuscularly.

The agents and compositions provided herein may be used alone or in combination with conventional therapeutic regimens such as surgery, irradiation, chemotherapy and/or bone marrow transplantation (autologous, syngeneic, allogeneic or unrelated).

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Representation of the TCR-CD3 complex. The intracytoplasmic CD3 immunoreceptor tyrosine-based activation motifs (ITAMs) are indicated as cylinders (adapted from "The T cell receptor facts book", MP Lefranc, G Lefranc, 2001).

FIG. 2: The design of successive generations of CARs. Schematic representation of the different generations of CARs (1G, first generation, 2G, second generation, 3G, third generation). The first generation contains extracellular scFvs and the cytoplasmic CD3ξ chain/ZAP70 mediating cytotoxicity, the second generation additionally CD28/PI3K promoting proliferation and the third generation furthermore 4-1BB or OX40/TRAF sustaining cell survival (Casucci, M. et al. (2011) 2: 378-382).

Figure 3:
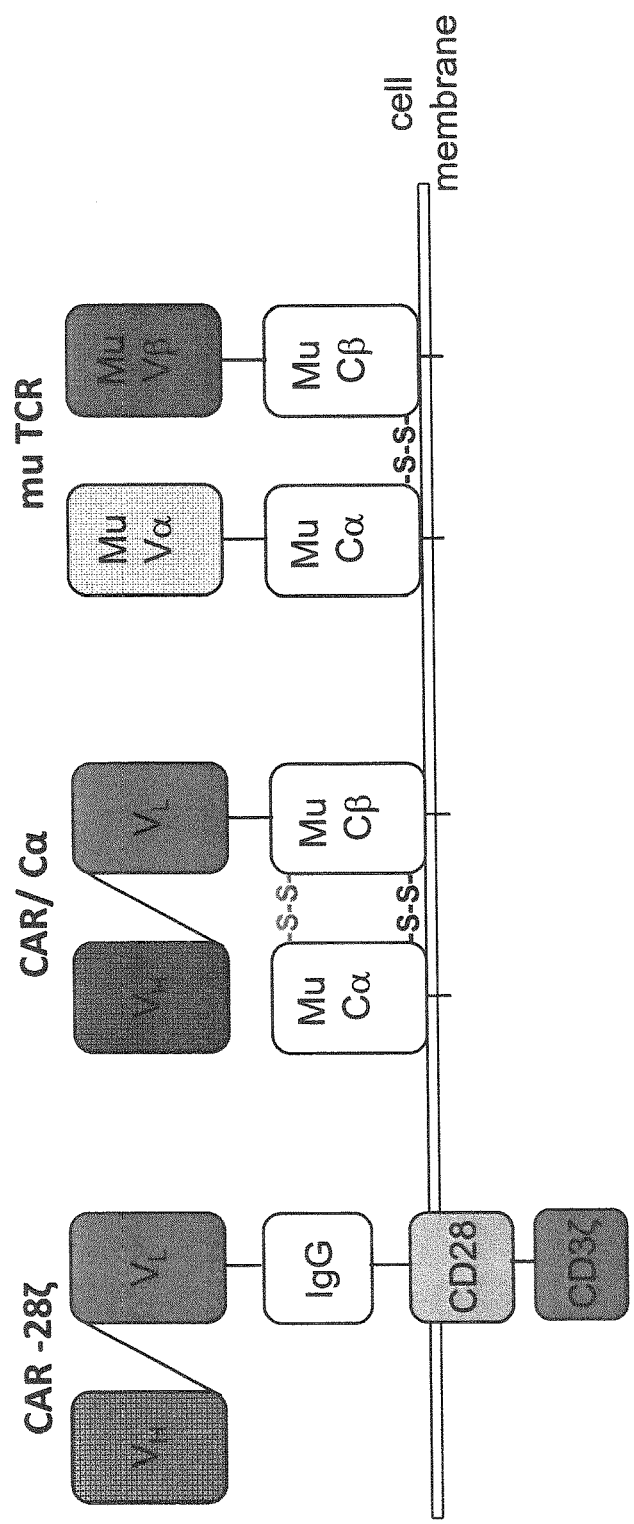
Figure 4:
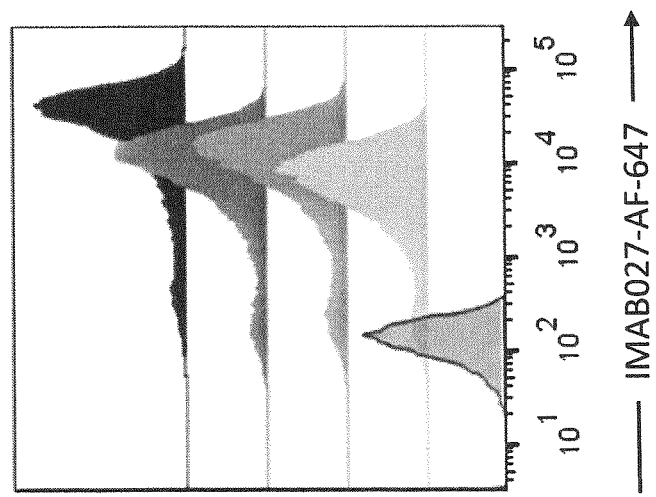
Figure 4:
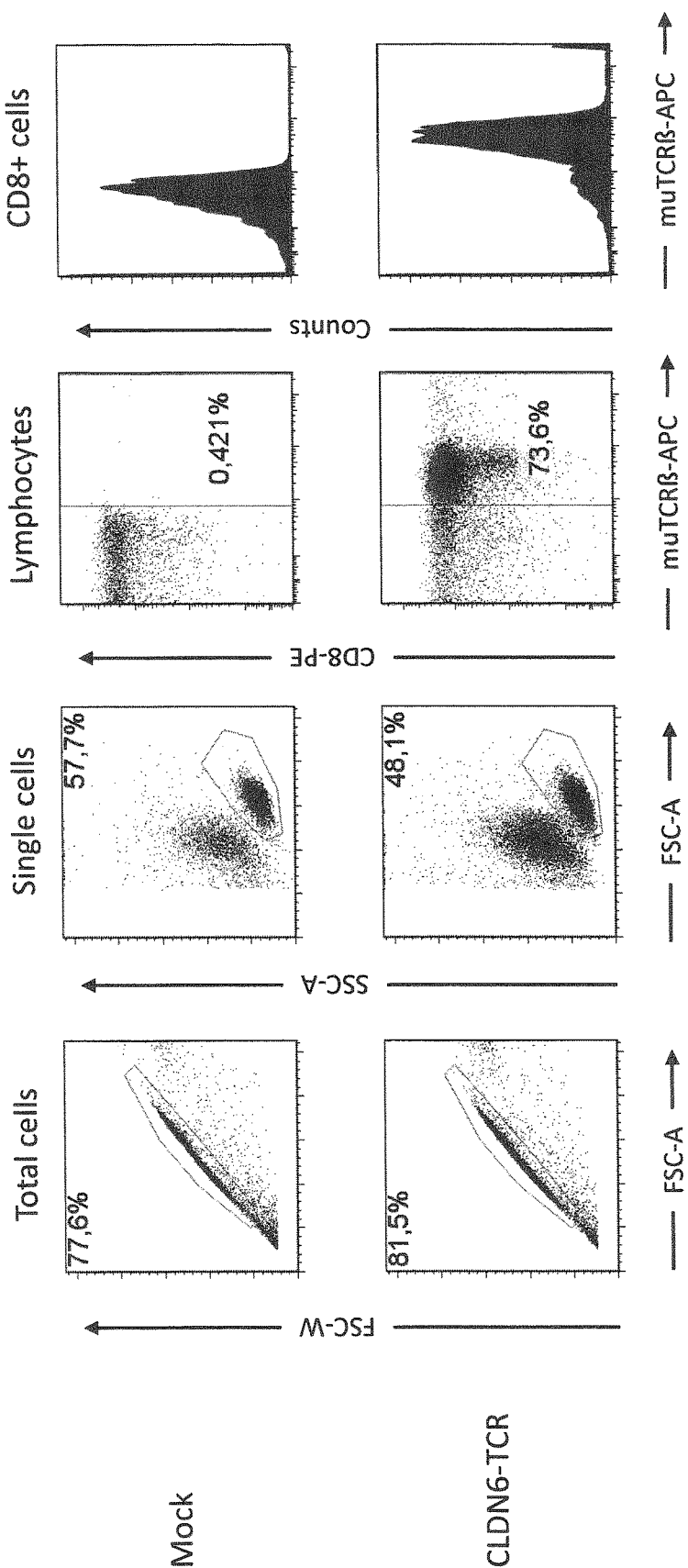
Figure 4:
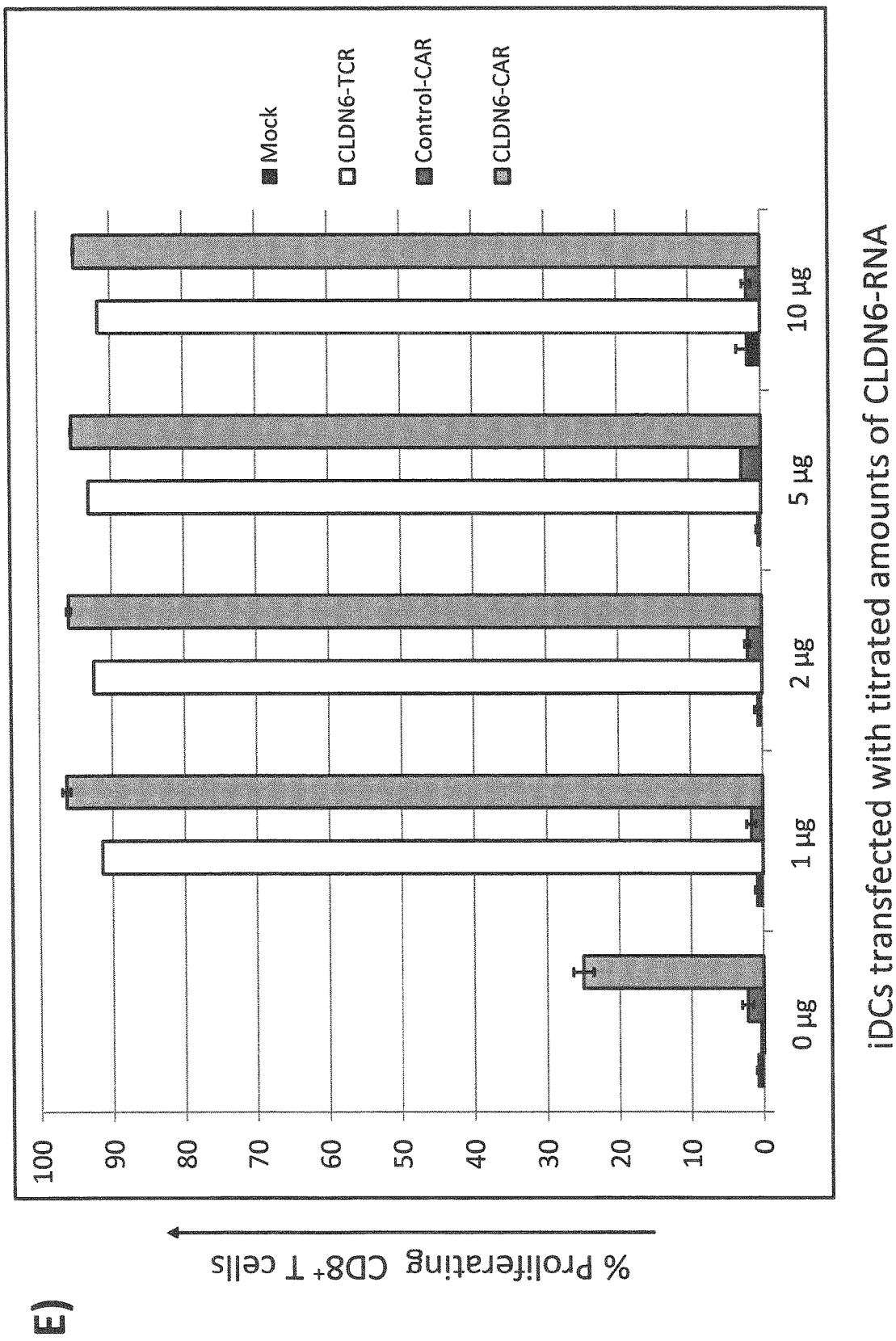

FIG. 3: Schematic representation of the different receptor formats for the redirection of T cells against an antigen. Left: a second generation CAR consisting of an antigen-specific scFv fragment, a IgG1-derived spacer domain, a CD28 costimulatory and a CD3ξ signaling domain (CAR-28ξ); middle: a novel CAR format based on the linkage of the scFv with the constant domain of the murine TCRβ chain and coexpression of the constant domain of the murine TCRα chain (CAR/Cα); right: a murine TCR composed of TCR α/β chains (mu, murine TCR);

FIG. 4: Proliferation of human CLDN6-specific T cells upon recognition to different amounts of antigen. Proliferation capacity of CFSE stained CLDN6-CAR engineered CD8+ T cells was analyzed after coculture with autologous iDCs transfected with indicated amounts of CLDN6 IVT RNA. (A) The CLDN6 expression on iDC transfected with titrated amounts of CLDN6 RNA was analyzed about 20 h after electroporation after staining with a Alexa-Fluor-647-conjugated CLDN6-specific antibody (IMAB027, Ganymed). Cells were gated on single cells. (B, C, D) CAR and TCR surface expression on CD8+ T cells transfected either with CLDN6-CAR or a control-CAR RNA or without RNA (mock) was analyzed after staining with fluorochrome-conjugated idiotype-specific antibodies detecting either the CLDN6-CAR (B) or the control-CAR (C). The surface expression of the murine CLDN6-specific TCR was assessed after staining with a murine TCR beta chain specific antibody (D). Cells were gated on single CD8+T lymphocytes. (E) After 96 h of coculture CFSE dilutions of CD8+ T cells were analyzed using flow cytometry. Positive control: CD8+ T cells transfected with a CLDN6-specific TCR; negative controls: CD8+ T cells transfected without RNA (mock); CD8+ T cells transfected with control-CAR RNA. (F) Representative dot plots of FACS analysis of receptor transfected T cells after coculture with 5 µg CLDN6 IVT RNA transfected autologous iDCs are shown. Numbers indicate percentages of parental populations.

Figure 5:
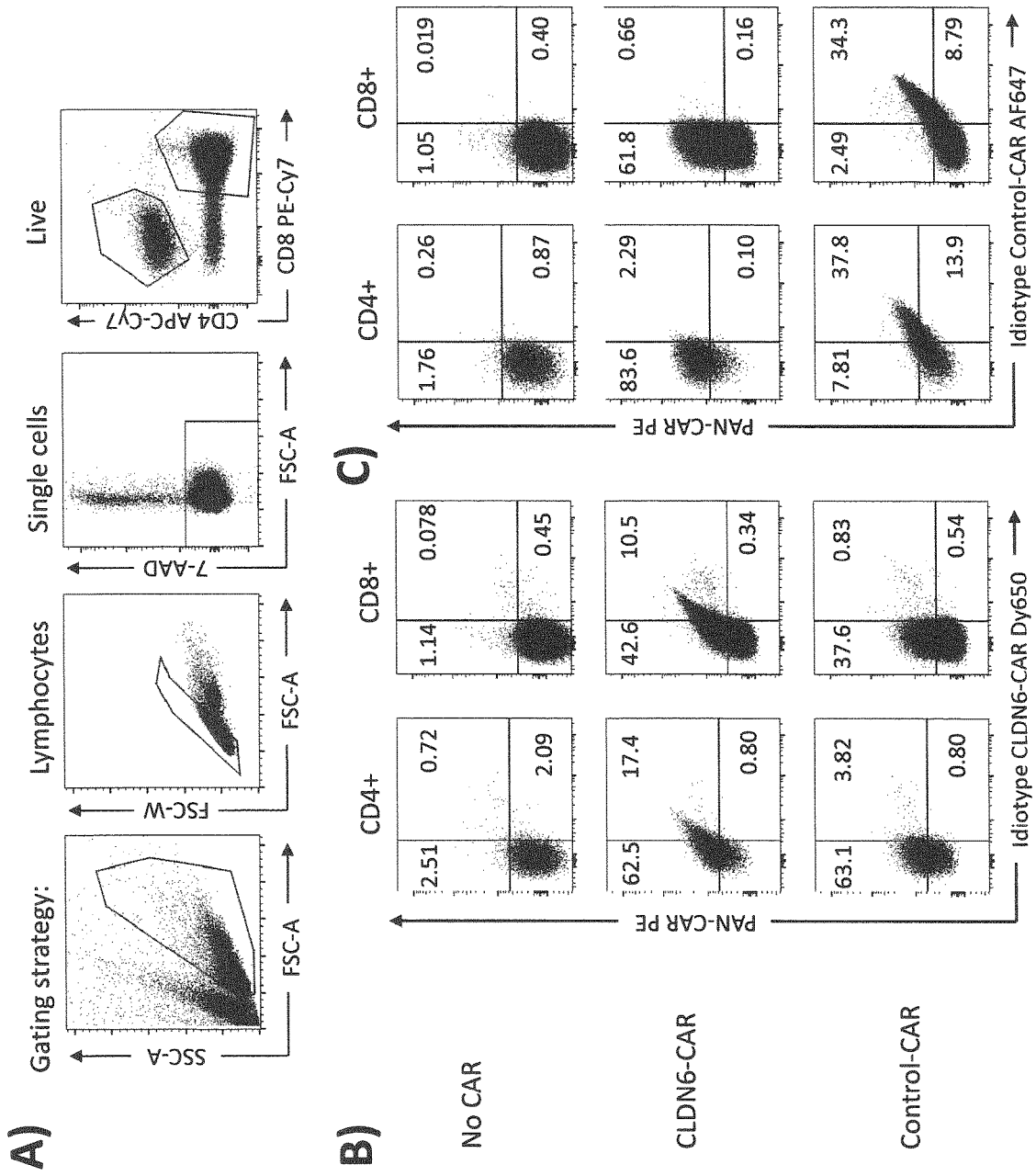

FIG. 5: Surface expression of the CLDN6-specific CAR constructs on murine T cells. Splenocytes were transduced with retroviral vectors containing either the CLDN6-CAR, the control-CAR or eGFP transgenes. 4 days after $2^{nd}$ transduction step, cells were stained with an APC-Cy7-conjugated anti-CD4, PE-Cy7-conjugated CD8, PE-conjugated anti-human IgG, which recognize all CAR molecules independent of their specificity and either DyLight650-conjugated anti-idiotype CLDN6 CAR (B) or AlexaFluor647-conjugated anti-idiotype control-CAR (C) antibodies, which recognized the respective CAR molecules. The general gating strategy is shown in (A). Numbers indicate percentages of parental populations.

Figure 6:
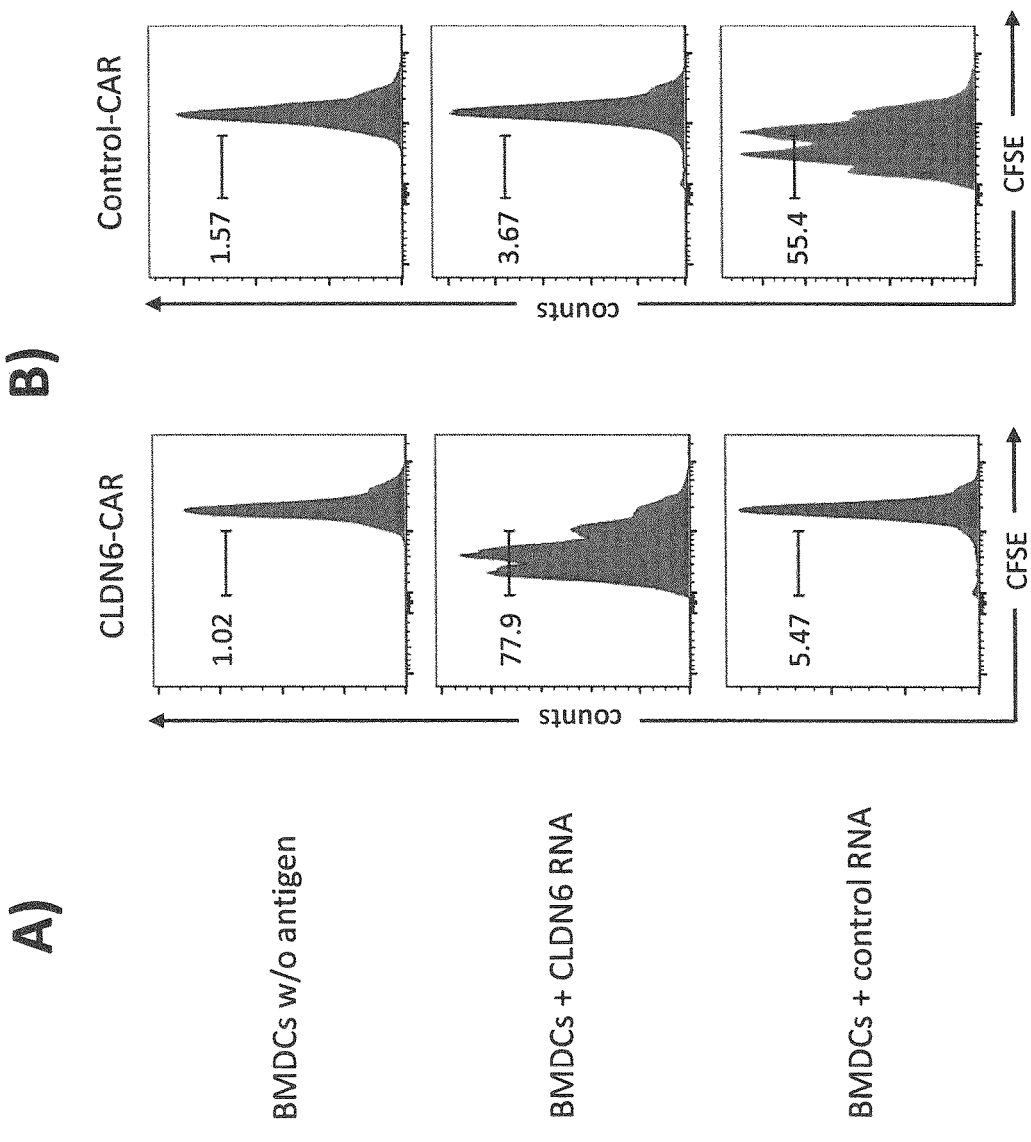

FIG. 6: Antigen-specific proliferation capacity of murine CAR-transduced T cells upon recognition to their respective antigens. CFSE stained CAR transduced T cells were co-cultured with either specific or irrelevant antigen transfected BMDCs (E:T ratio 8:1) and as negative control T cells were cultured without BMDCs. After 48 h, cells were harvested and CFSE staining of CLDN6-CAR transduced (A) and control-CAR transduced (B) T cells were measured using flow cytometry. Numbers indicated percentage of expanded cells of parental population (single cell gate).

Figure 7:
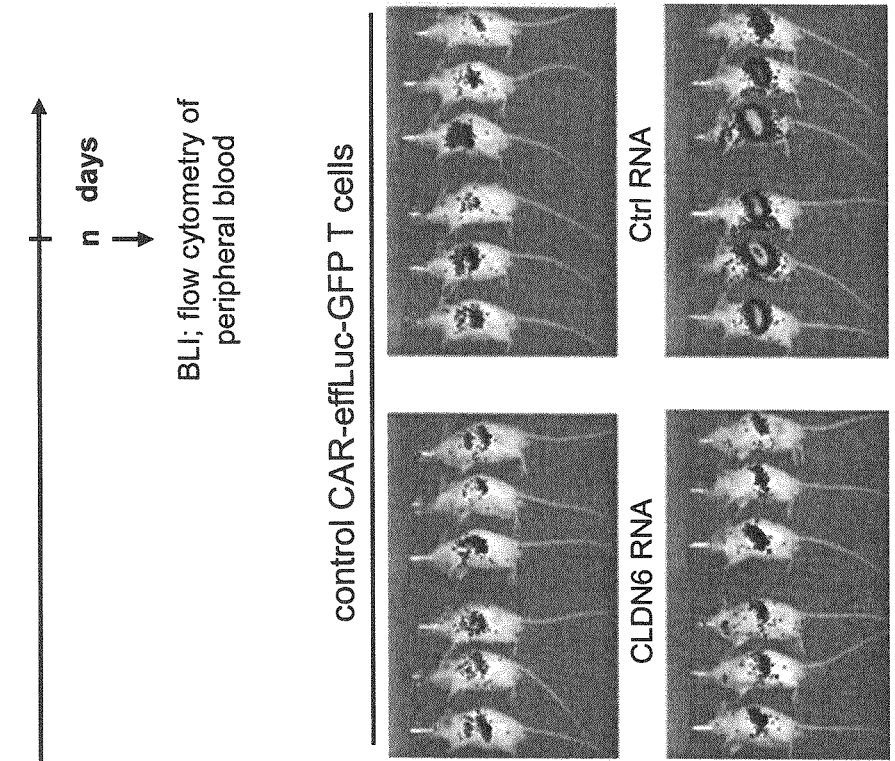
Figure 7:
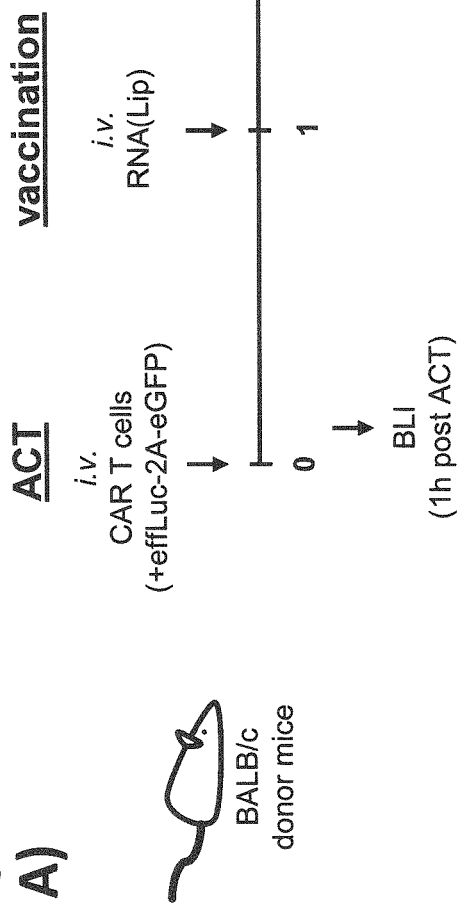
Figure 7:
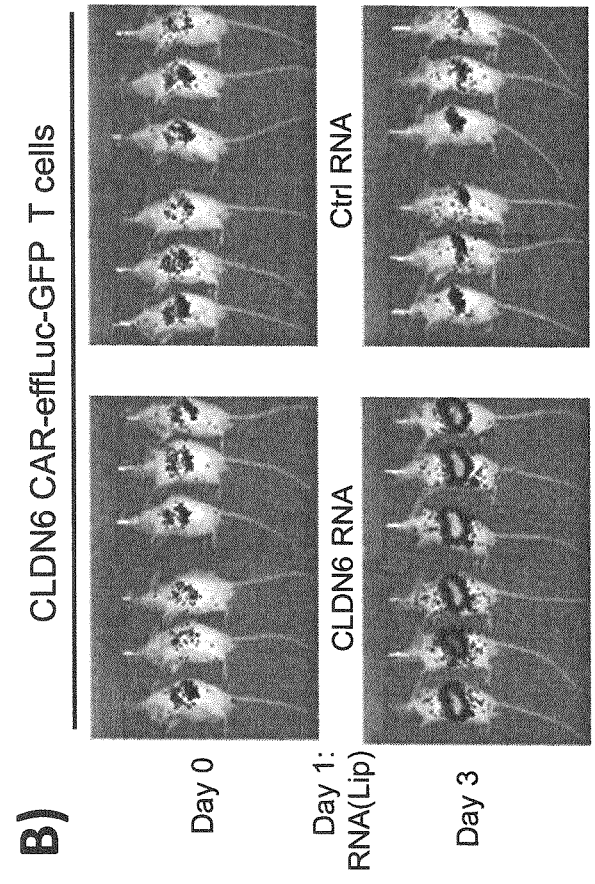
Figure 7:
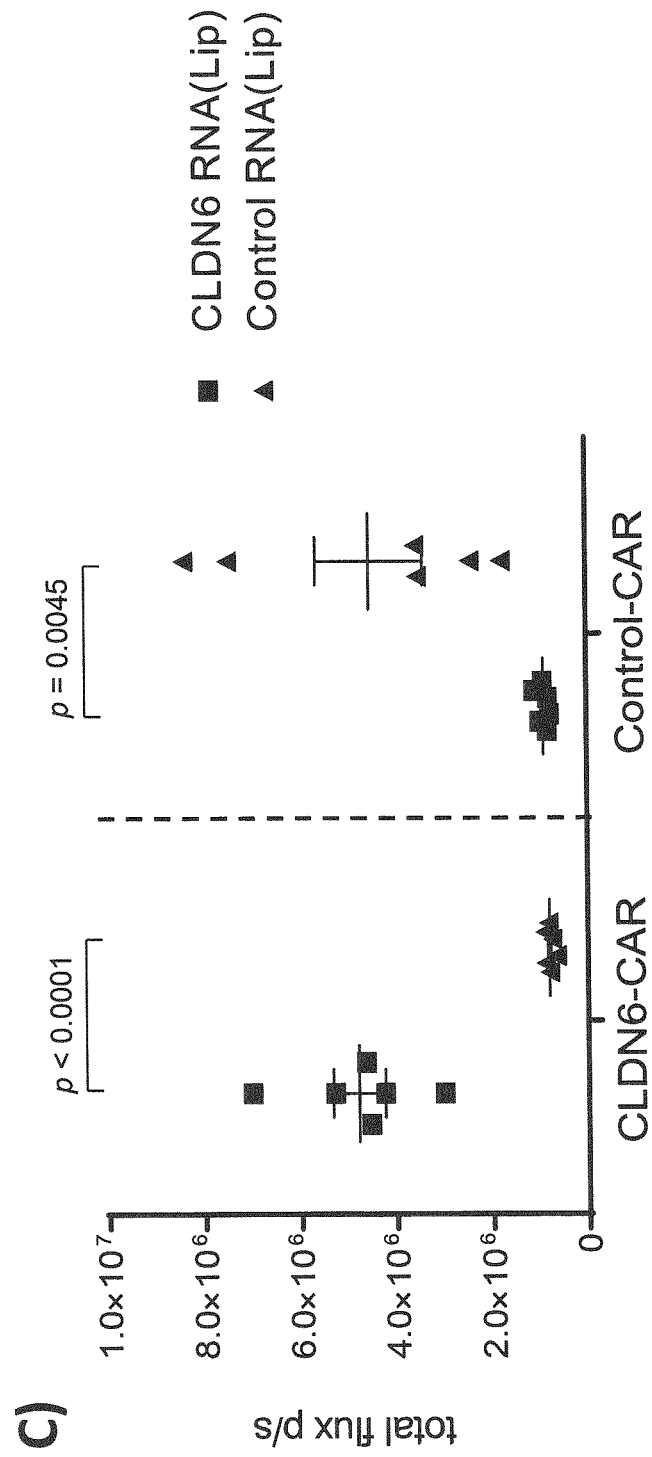

FIG. 7: Antigen-specific in situ expansion of CLDN6-CAR T cells in immunocompetent mice after RNA(Lip) vaccination. BALB/c-mice (n=12/group) were i.v. engrafted with $5 \times 10^6$ CLDN6-CAR-effLuc-GFP or control CAR-effLuc-eGFP transduced BALB/c-Thy1.1$^+$ T cells, respectively. One day (day 1) after ACT, half of the mice (n=6) in each group were treated i.v. with RNA(F12-Lip) comprising 25 µg CLDN6 RNA, whereas the other half were treated with RNA(Lip) comprising 25 µg control antigen RNA. In both experimental groups (ACT of CLDN6-CAR vs control CAR-T cells), mice treated with the respective non-target antigen-encoding RNA(Lip) served as negative controls. In vivo-luminescence intensities were measured 1 h (day 0) and 72 h (day 3) post ACT. (A) Schematic overview of the experimental set-up. (B) Bioluminescence imaging (BLI) of mice in lateral position at various time points after ACT and treatment with RNA(Lip) as indicated. Off-color images represent light intensity (black, least intense; white up to dark-grey, most intense) which was superimposed over the greyscale reference photo. (C) At day 3 after RNA(Lip) treatment (peak of CAR T cell expansion) light emission of mice was assessed (mean±SEM). Differences in light emission of different treated groups were analyzed using two-tailed t-test including welch-correction.

Figure 8:
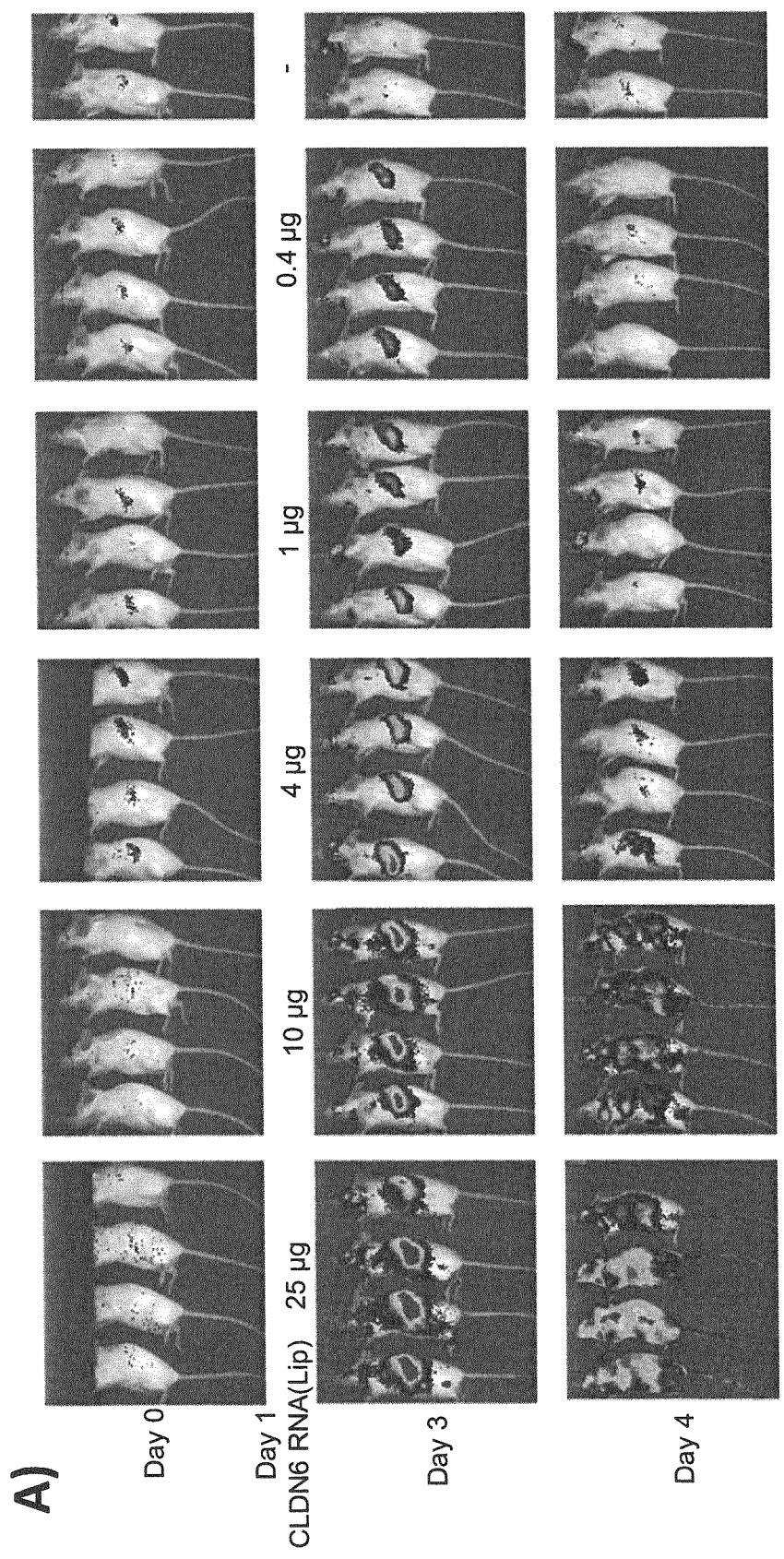
Figure 8:
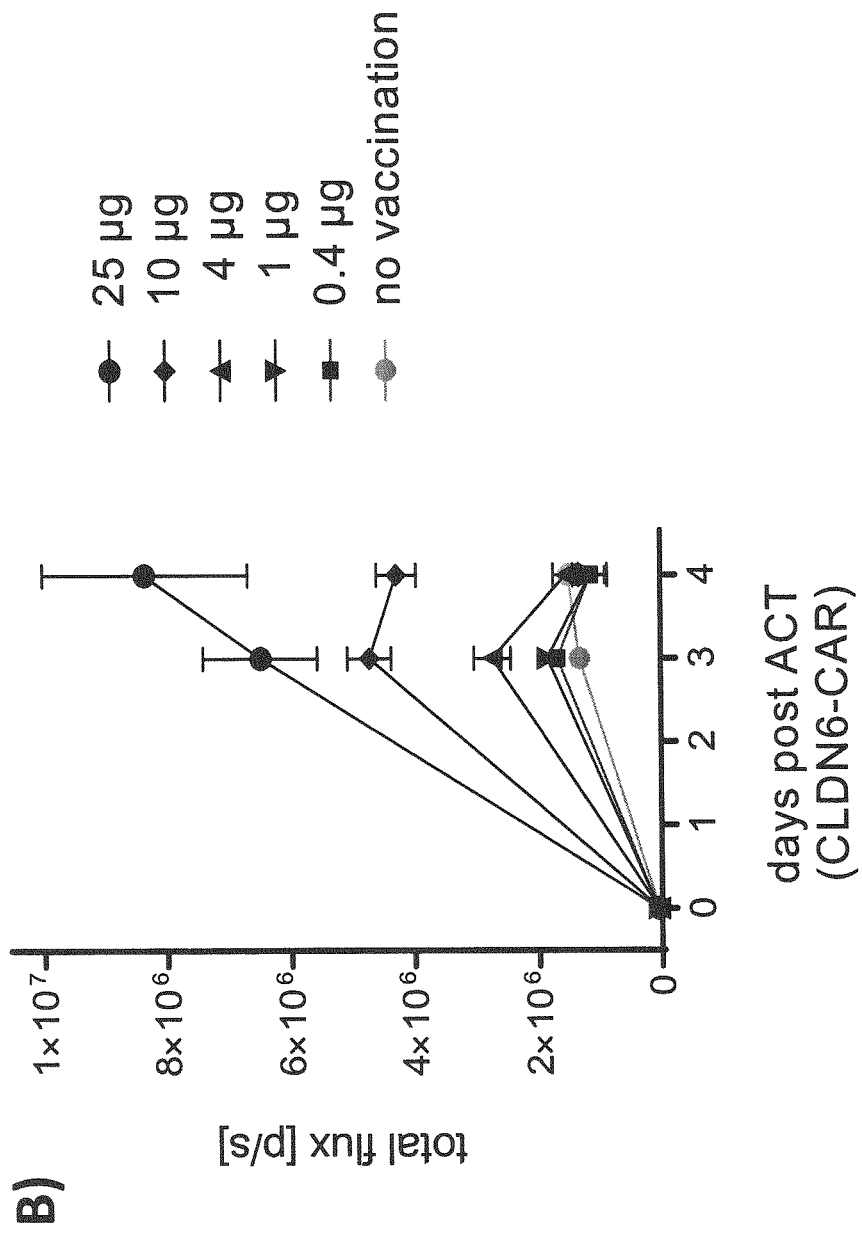
Figure 8:
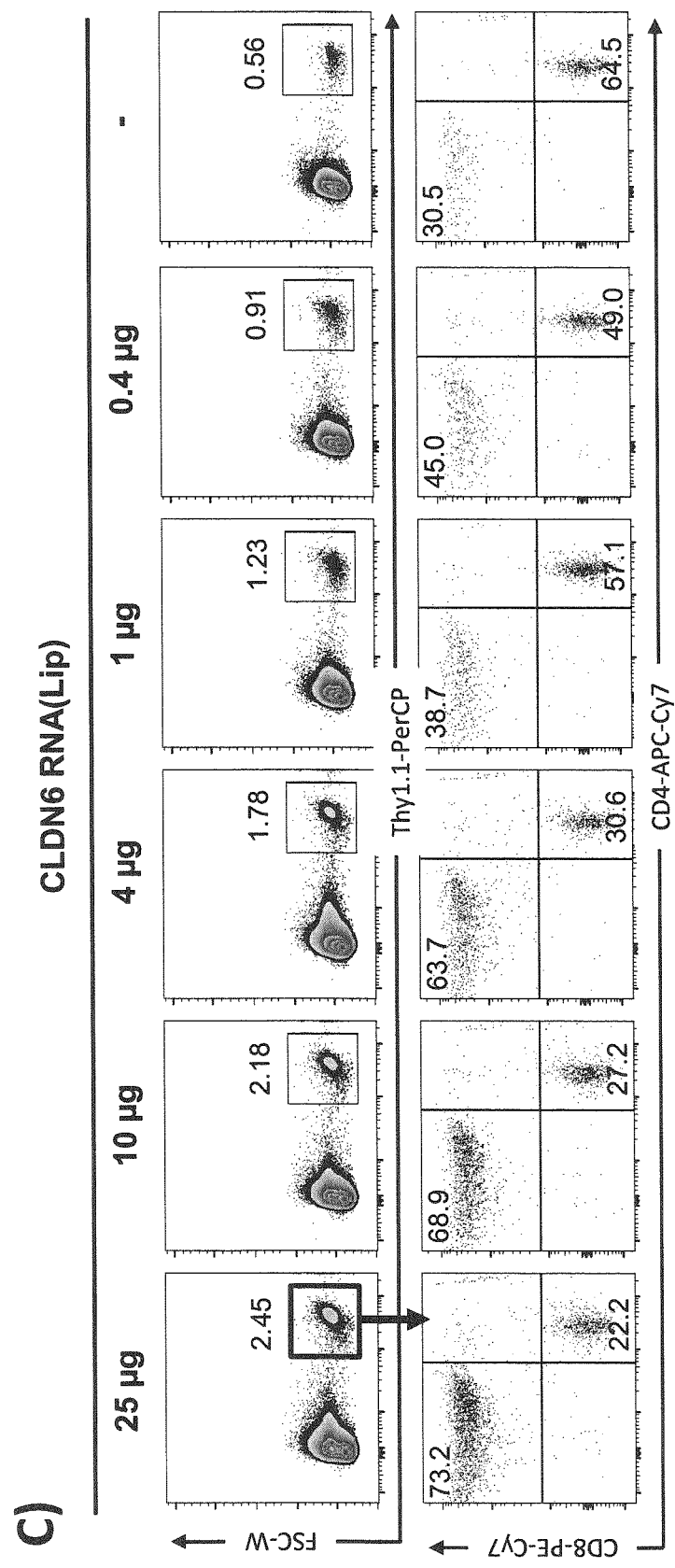

FIG. 8: In vivo expansion of CAR T cells by RNA(Lip) vaccination is dependent on amount of RNA. Different doses of RNA(Lip) comprising CLDN6 RNA were applied by i.v. injection into BALB/c mice (n=4/group/RNA amount) engrafted with Thy1.1$^+$ CLDN6-CAR T cells 1 day post ACT as described in FIG. 7. BALB/c mice (n=2) which received CLDN6-CAR T cells but no RNA(Lip) served as control. Expansion of CLDN6-CAR T cells was monitored in situ using luciferase based bioluminescence imaging and in peripheral blood at day 3 post ACT using flow cytometry. (A) Bioluminescence imaging of mice in lateral position at various time points after ACT and treatment with RNA(Lip) as indicated. Off-color images represent light intensity (black, least intense; white up to dark-grey, most intense) which was superimposed over the greyscale reference images. (B) Time course of in vivo bioluminescence data (n=4, control group n=2; mean±SEM). (C) Frequencies of adoptively transferred Thy1.1$^+$ T cells and the CD4 and CD8 T cell composition of these cells were assessed via flow cytometry in peripheral blood 48 h after vaccination using PerCP-conjugated murine CD90.1/Thy1.1, APC-Cy7-conjugated murine CD4 and PE-Cy7-conjugated murine CD8a monoclonal antibodies. For each treatment, a representative zebra blot as well as dot plot are shown. Numbers indicate percentage of parental populations (D and E). Flow cytometric results of all mice are summarized (mean±SD).

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Peripheral Blood Mononuclear Cells (PBMCs), Monocytes and Dendritic Cells (DCs)

PBMCs were isolated by Ficoll-Hypaque (Amersham Biosciences, Uppsala, Sweden) density gradient centrifugation from buffy coats. Monocytes were enriched with anti-CD14 microbeads (Miltenyi Biotech, Bergisch-Gladbach, Germany). Immature DCs (iDCs) were obtained by differentiating monocytes for 5 days in cytokine-supplemented culture medium as described in Kreiter et al. (2007), Cancer Immunol. Immunother., CII, 56, 1577-87.

Isolation and Activation of Spleen Cells

Splenocytes were isolated from naïve C57B16 mice and $1*10^7$ were transferred into culture media (RPMI1640) and were pre-activated 24 h with 2 µg/ml anti-CD3 (eBioscience), 1 µg/mL anti-CD28 (Novus Biologicals) and 5 ng/mL recombinant human (rh) IL-7 and 10 ng/mL rh IL-15 (Miltenyi).

Retroviral Transduction of Murine Splenocytes

Non tissue plates were coated with 2.1 µg/cm$^2$ RetroNectin (Clontech) over night at 4° C. After coating, RetroNectin were removed and then blocked 30 min at room temperature with 500 µl PBS/2% BSA [w/v] for each well. BSA solution was removed and wells were washed once with PBS. PBS was replaced with retroviral (MLV-E) vectors containing either the CLDN6-CAR, the Control-CAR or eGFP transgenes and plate were centrifuged 15 min 1300×g. This process was iterated 2 more times with fresh viral culture supernatant. Wells were then carefully flushed with PBS before $1 \times 10^6$ 24 h preactivated murine splenocytes were incubated on coated wells. After 4 h incubation, viral supernatants were added and spin transduction was performed with 300×g 37° C. and cells were incubated 1 additional hour in incubator before viral supernatant was replaced with culture media containing 5 ng/mL IL-7 and 10 ng/mL IL-15. The whole transduction procedure was repeated one day later. After the second transduction step, viral supernatant were replaced by freshly culture media. For CFSE based proliferation assay, cells were harvested on day 7 after isolation and were ficoll cleaned with Ficoll-Paque PREMIUM (1.084) prior CFSE staining.

Generation of In Vitro Transcribed (IVT) RNA and Transfer into Cells

Generation of IVT RNA was performed as described previously (Holtkamp, S. et al. (2006), Blood 108, 4009-4017) and indicated amounts of IVT RNA (CLDN6 or control-antigen into murine BMDCs: 6 µg; CARs into human T cells: 15-20 µg; TCRs into human T cells: 20 µg each chain; CLDN6 or gp100 into iDCs: 10 µg) were added to cells suspended in 250 µL X-VIVO 15 medium (Lonza, Basel, Switzerland) in a pre-cooled 4-mm gap sterile electroporation cuvette (Peqlab). Electroporation was performed with an ECM 830 Square Wave Electroporation System apparatus (BTX) (murine BMDCs: 400 V, 3 ms, 1 pulse, human T cells 500 V, 3 ms, 1 pulse, human iDCs: 300 V, 12 ms, 1 pulse).

CFSE Based Proliferation Assay

Murine cells were labeled with 5 µM CFSE, human T cells with 0.8 µM. Labeled cells were washed and co-cultured with IVT-RNA-transfected cells APCs (e.g. BMDCs or iDCs) at indicated effector target ratios. After 2 days or 4 days of co-culture, cells were harvested and proliferation was analyzed by flow cytometry based on the progressive halving of CFSE fluorescence within daughter cells following cell divisions.

Flow Cytometric Analyses

Cell surface expression of transduced CARs was analyzed using a fluorochrome-conjugated idiotype-specific antibodies (Ganymed pharmaceuticals) recognizing the scFv fragment and human IgG-PE antibodies which recognize the IgG1-linker (contained in all CAR constructs). Cell surface expression of CLDN6 was performed using the Alexa-Fluor-647-conjugated CLDN6-specific antibody IMAB027 (Ganymed pharmaceuticals). Flow cytometric analysis was performed on a FACS CANTO II flow cytometer using the FACS Diva software (BD Biosciences).

Animals

Mice were purchased from commercial providers. Age (8-10 weeks old) and sex (male or female) matched animals were used throughout the experiments.

Retroviral Gene Manipulation and Preparation CAR T Cells for Adoptive T Cell Transfer Splenocytes of nave BALB/c-Thy1.1$^+$ were isolated and pre-activated by 2 µg/mL Concanavalin A (Sigma-Aldrich) in the presence of 5 ng/mL rh IL-7 and 1.5-10 ng/mL rh IL-15 (Miltenyi). Pre-activated cells were transduced as described in section "Retroviral transduction of murine splenocytes". Retroviral vectors containing either control-CAR or CLDN6-CAR encoded as well enhanced firefly luciferase (effLuc; Rabinovich B. A. et al. (2008) Proc. Natl. Acad. Sci. U.S.A 105, 14342-14346) and eGFP (enhanced green fluorescence protein) reporter gene, which expressed separately using 'self-cleaving' T2A-elements (Szymczak A. L. et al. (2004) Nat. Biotechnol. 22, 589-594). After ficoll cleaning, cells were washed twice with PBS to remove serum proteins and were then prepared for adoptive cell transfer (ACT).

Generation of Liposomal Formulated IVT RNA (RNA(Lip))

Different amounts of CLDN6 or control-IVT RNA were complexed with F12-liposomes comprising DOTMA/DOPE (1,2-di-O-octadecenyl-3-trimethylammonium propane/1,2-Dioleoyl-sn-glycero-3-phosphoethanolamine (2:1 mol:mol)) as previously described in WO2013/143683.

Mouse Experiments $5 \times 10^6$ CAR-T2A-effLuc-T2A-eGFP transduced BALB/c-Thy1.1$^+$ T cells in 200 µL were intravenously (i.v.) transferred into each BALB/c donor mice. Subsequently, mice were i.v. vaccinated with an F12:RNA ratio of 1.3:2 of RNA(Lip) 24 hours after adoptive T cells transfer (ACT). Peripheral blood donation and whole body bioluminescence imaging were performed.

In Vivo Luciferase Imaging (BLI)

Expansion and distribution of CAR-effLuc-GFP transduced T cells were evaluated by in vivo bioluminescence imaging using the IVIS Lumina imaging system (Caliper Life Sciences). Briefly, an aqueous solution of D-luciferin (80 mg/kg body weight; Perkin Elmer) was injected i.p. 1 h (day 0), 72 h (day 3) and 96 h (day 4) after ACT. 5 min thereafter, emitted photons were quantified (integration time of 1 min) In vivo bioluminescence in regions of interest (ROI) were quantified as average radiance (photons/sec/cm2/sr) using IVIS Living Image 4.0 Software. The intensity of transmitted light originating from luciferase expressing cells within the animal was represented as a greyscale image, where black is the least intense and white to dark-grey the most intense bioluminescence signal. Greyscale reference images of mice were obtained under LED low light illumination. The images were superimposed using the Living Image 4.0 software.

Flow Cytometry of Peripheral Blood of Mice

Cell composition of transferred Thy1.1$^+$ T cells were assessed 72 h (day3) after ACT in hypothonicly lysed peripheral blood samples (ACK buffer; GIBCO). Fluoro-chrome-coupled monoclonal antibodies detecting murine CD90.1/Thy1.1 (BD Pharmingen), CD8α (eBioscience) and CD4 (BD Pharmingen) were used. Flow cytometric data were acquired on a FACS-Canto II analytical flow cytometer and analyzed by using FlowJo X (Tree Star) software.

Example 2: Expansion of CAR Engineered T Cells with IVT RNA Pulsed APCs In Vitro An important prerequisite for the proliferation and persistence of CAR-engineered T cells in the patient is the presence of antigen as demonstrated by promising clinical trial results of CD19-specific CARs in hematologic malignancies. In analogy to the expansion of endogenous T cells by RNA immunization via TCR stimulation by MHC-peptide complexes, we wanted to analyze, if adoptively transferred CAR T cells could also be expanded using Liposome mediated RNA-vaccination of target cells to provide the natural surface expressed antigen for CAR T cell stimulation. Such a 'switch' could make it possible to initially transfer small amounts of CAR-engineered T cells into the patients. If this transfer resulted in no severe side effects in patients, engineered T cells could then be expanded with liposomal formulated RNA. Furthermore this method could be in some circumstances an opportunity for tumor patients to avoid chemotherapy that artificially creates space for adoptive T cell transfer.

We evaluated the expansion concept in vitro for a CAR that specifically targets the tumor antigen CLDN6. The CLDN6-CAR represents a classical 2nd generation CAR that contains the signaling and costimulatory moieties of CD3ξ and CD28, respectively. A deletion of the lck binding moiety in the CD28 endodomain abrogates IL-2 secretion upon CAR engagement to prevent induction of regulatory T cells (Kofler D. M. et al., (2011) Molecular Therapy 19 (4), 760-767). A modification of the IgG1 Fc 'spacer' domain in the extracellular moiety of the CAR avoids 'off-target' activation and unintended initiation of an innate immune response (Hombach A. et al., (2010) Gene Therapy 17, 1206-1213).

First we wanted to analyze, if CAR-engineered human T cells could also be expanded using RNA-transfected target cells to provide natural CLND6 for CAR T cell stimulation. A CFSE based in vitro co-culture assay was performed using CLDN6-CAR-RNA transfected human CD8+ T cells together with autologous iDCs transfected with titrated amounts of CLDN6 IVT RNA. The resulting dose-dependent CLDN6 surface expression was assessed by flow cytometry after staining with a CLDN6-specific antibody (FIG. 4A). As a positive control CD8+ T cells were transfected with RNA encoding a HLA-A*0201-restricted CLDN6-specific murine TCR and as a negative control a control CAR was included. The surface expression of the transfected CARs and the TCR was analyzed after staining with idiotype-specific and murine TCR-beta-specific antibodies (FIG. 4B, C, D). After four days of coculture, the antigen-specific proliferation of all receptor-transfected and CFSE-labeled CD8+ T cells in response to CLDN6-expressing iDCs was analyzed based on the progressive halving of CFSE fluorescence by flow cytometry. The CLDN6-CAR mediated proliferation of nearly all CD8+ T cells in response to CLDN6-transfected target cells even at low antigen concentration (1 µg CLDN6 RNA; 95%). The percentage of proliferating CLDN6-CAR T cells was even higher than the proportion of CLDN6-TCR transfected T cells that served as a positive control accounting for about 90%, while the control-CAR did not induce proliferation upon CLDN6 antigen contact (FIG. 4E, F). This result confirmed that CAR molecules can strongly induce proliferation in T cells in vitro after coculture with RNA-transfected iDCs, the cell population that is mainly responsible for RNA uptake in the lymph nodes in vivo after RNA vaccination.

In order to translate our strategy in an in vivo experiment, we first analyzed the proliferative capacity of murine CLDN6-CAR-expressing T cells using a similar experimental setup. To that aim splenocytes of C57Bl/6 mice were transduced with retroviral vectors containing either the CLDN6-CAR or a control CAR or no transgene.

As CARs provide MHC or HLA independent scFv-mediated antigen-binding they are functional in both CD4+ and CD8+ T cells. Therefore, we first analyzed the CAR surface expression on CD4+ and CD8+ T cells after retroviral transduction of both CARs on murine splenocytes (FIG. 5). Both molecules could be detected on the surface of CD4+ as well as on CD8+ T cells using CAR-specific antibodies (anti-idiotype specific antibodies and PAN-CAR antibody which recognize ubiquitously occurred IgG1-Fc spacer region). A CFSE-based in vitro proliferation assay was performed using either CLDN6-CAR or control CAR-transduced splenocytes together with CLDN6 or control RNA-transfected BMDCs (FIG. 6). The CLDN6-CAR showed strong proliferative properties in response to CLDN6 transfected target cells (about 78%), while no proliferation was observed upon recognition of target cells which expressed the antigen recognized by the control CAR. Vice versa the control CAR initiated proliferation (55.4%) of transduced T cells exclusively in response to target cells expressing the respective antigen, while no proliferation could be observed after coculture of CLDN6-expression target cells.

This result confirmed the functionality of the CLDN6-CAR in murine T cells in vitro and demonstrated that murine CLDN6-CAR T cells are able to strongly proliferate in response to murine BMDCs expressing the human CLDN6 antigen after RNA transfer. This provides the basis for the testing of our proposed strategy in an in vivo environment using adoptive transfer of murine CAR-expressing T cells combined with liposomal formulated RNA-vaccination in a syngenic animal model.

Example 3: Expansion of CAR Engineered T Cells with IVT RNA Pulsed APCs In Vivo

In order to test this innovative concept in a physiological setting, we established a syngeneic mouse model which is fully immunocompetent and, hence, more closely reflects the immune status of the patients and allows for analyzing persistence of transferred CAR T cells.

An antigen e.g. CLDN6-encoding, liposomally formulated RNA (RNA(Lip)) shall be used to expand CAR T cells in vivo in a controlled fashion. RNA(Lip) selectively targets APCs like DCs in secondary lymphoid organs, the spleen in particular. The interaction of CAR-T cells with APCs that ectopically express CLDN6 after RNA(Lip) uptake is expected to support adequate CAR-T cell activation and proliferation by providing natural co-stimulation in situ. To facilitate the expansion and fate of CAR-T cells in vivo, the pES12.6-CLDN6-CAR vector and a control CAR vector were modified to express luciferase (effLuc) and eGFP reporter genes downstream of the respective CAR separated by viral T2A sequences. Of note, surface expression and antigen specificity of CLDN6-CAR and the control-CAR were not significantly affected by coexpression of luciferase and GFP in CAR-transduced murine T cells (data not shown).

BALB/c mice were engrafted with 5×10⁶ CAR-reporter transduced congenic Thy1.1⁺ murine bulk T cells (approx. 2.5×10⁸ cells/kg body weight) without prior lympho-depletion. 200 µL RNA(Lip) containing either 25 µg human CLDN6 or a control RNA were administered retroorbital into mice 1 day after adoptive CAR-T cell transfer (FIG. 7A). CAR-T cells were then tracked in vivo by intraperitoneal administration of 1.66 mg D-Luciferin solution per mouse. 1 hour after ACT, most of the CAR-T cells were already found in the spleen. A significant (up to 6-fold) increase in total flux was induced by treatment with 25 µg RNA(Lip) as detected by bioluminescence imaging 3 days after ACT (FIG. 7B+C). This effect was observed for mice having received CLDN6-CAR T cells after treatment with CLDN6-encoding RNA(Lip) as well as for mice having received control CAR-T cells after treatment with control RNA-encoding RNA(Lip), but not in the respective control groups. These data demonstrate that CAR-T cells can successfully be expanded in situ in a highly antigen-specific manner. In addition, clinical monitoring of mice for changes in body weight and general health status did not reveal any obvious negative effects of CAR-T cell transfer and subsequent treatment with RNA(Lip) (data not shown).

After having demonstrated that CAR-T cells can successfully be expanded in situ using RNA(Lip) encoding the respective antigen (proof of principle), we investigated whether this effect correlates with the amount of RNA(Lip) used in a dose response study. For this purpose CLDN6-CAR transduced murine Thy1.1⁺ T cell-engrafted BALB/c mice were treated (as described above) with 0.4-25 µg of CLDN6-RNA(Lip). A dose-dependent expansion of CLDN6-CAR T cells could be observed in situ via BLI. Even the administration of low dose of CLDN6-encoding RNA (0.4-1 µg/mouse) led to increase in light emission in mice compared to the non-treated group (FIG. 8A+B). Beside the change in bioluminescence after RNA(Lip) vaccination, the frequencies of adoptively transferred CLDN6-

CAR Thy1.1+ T cells showed an approx. 4.2-fold increase in peripheral blood 3 days post ACT compared to non-vaccinated mice (no vaccination: 0.63±0.09% Thy1.1+ T cells; 25 μg CLDN6-RNA(Lip)-vaccination: 2.65±0.38% Thy1.1+ T cells; mean±SD) (FIG. 8C+D). Expanded Thy1.1+ T cells detected in peripheral blood were mainly cytotoxic CD8±CAR-T cells, i.e. the cell type which can directly execute anti-tumor functions in patients compared to non-vaccinated mice where CD4+ T cells prevail (FIG. 8E). The change in subpopulations was clearly concentration-dependent.

These data strongly support the idea that controlled CAR-T cell expansion directly in the patient using RNA (Lip) technology is feasible.

The invention claimed is:

1. A method for stimulating an immune response to a target cell population or target tissue expressing an antigen in a mammal, the method consisting of:
   (a) systemically administering to the mammal T cells in a pharmaceutically acceptable carrier, diluent, buffer, preservative, or excipient, wherein the T cells are genetically modified to express a chimeric antigen receptor (CAR) targeted to the antigen; and
   (b) systemically administering at least one nucleic acid encoding the antigen or a variant thereof, wherein the nucleic acid is in vitro transcribed RNA disposed in liposomes, in a pharmaceutically acceptable carrier, diluent, buffer, preservative, or excipient.

2. The method of claim 1, wherein the immune response is a T cell-mediated immune response.

3. The method of claim 1, wherein the immune response is an anti-tumor immune response and the target cell population or target tissue is tumor cells or tumor tissue.

4. The method of claim 1, wherein the antigen is a tumor antigen.

5. The method of claim 1, wherein the antigen is a pathogen antigen.

6. The method of claim 1, wherein the nucleic acid encoding the antigen or variant thereof is expressed in cells of the mammal to provide the antigen or variant thereof.

7. The method of claim 6, wherein expression of the antigen or variant thereof is at the cell surface.

8. The method of claim 1, wherein the nucleic acid encoding the antigen or variant thereof is transiently expressed in cells of the mammal.

9. The method of claim 1, wherein systemic administration of the nucleic acid encoding the antigen or variant thereof stimulates expression of the antigen or variant thereof in antigen presenting cells.

10. The method of claim 9, wherein the antigen presenting cells are selected from the group consisting of dendritic cells, macrophages and B cells.

11. The method of claim 1, wherein the nucleic acid encoding the antigen or variant thereof is expressed in cells of the mammal to provide the antigen or variant thereof for binding by the T cells genetically modified to express the CAR, said binding resulting in stimulation, priming and/or expansion of the T cells genetically modified to express the CAR.

12. The method of claim 1, wherein the T cells genetically modified to express the CAR are T cells or T cell progenitors which are obtained from the mammal and transfected with a nucleic acid encoding the CAR.

13. The method of claim 1, wherein the T cells genetically modified to express a CAR are stably or transiently transfected with nucleic acid encoding the CAR.

14. The method of claim 1, wherein the T cells are from the mammal to which the T cells genetically modified to express a CAR and the nucleic acid encoding the antigen or variant thereof are administered.

15. The method of claim 1, wherein the T cells are from a mammal which is different than the mammal to which the T cells genetically modified to express a CAR and the nucleic acid encoding the antigen or variant thereof are administered.

16. The method of claim 1, wherein the liposomes comprise DOTMA and DOPE or DOTMA and cholesterol.

17. A method of treating a mammal having a disease, disorder or condition associated with expression or elevated expression of an antigen, the method consisting of:
   (a) systemically administering to the mammal T cells in a pharmaceutically acceptable carrier, diluent, buffer, preservative, or excipient, wherein the T cells are genetically modified to express a chimeric antigen receptor (CAR) targeted to the antigen; and
   (b) systemically administering a nucleic acid encoding the antigen or a variant thereof, wherein the nucleic acid is in vitro transcribed RNA disposed in liposomes, in a pharmaceutically acceptable carrier, diluent, buffer, preservative, or excipient.

18. The method of claim 17, wherein the disease, disorder or condition is cancer.

* * * * *

UNITED STATES PATENT AND TRADEMARK OFFICE
CERTIFICATE OF CORRECTION

PATENT NO. : 10,799,534 B2
APPLICATION NO. : 15/573045
DATED : October 13, 2020
INVENTOR(S) : Ugur Sahin et al.

Page 1 of 1

It is certified that error appears in the above-identified patent and that said Letters Patent is hereby corrected as shown below:

On the Title Page

The following should be deleted:
Related U.S. Application Data
(63) Continuation of application No. PCT/EP2015/060356, filed on May 11, 2015.

The following should be added:
(30) Foreign Application Priority Data
May 11, 2015 (WO) .................. PCT/EP2015/060356

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 8

<210> SEQ ID NO 1
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 220
<212> TYPE: PRT
<213> ORGANISM: Homo sapiens

<400> SEQUENCE: 2
```

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 3
<211> LENGTH: 220
<212> TYPE: PRT
<213> ORGANISM: Homo sapiens

<400> SEQUENCE: 3

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160
```

```
Gly Ala Ser Leu Tyr Leu Gly Trp Ala Ala Ser Gly Leu Leu Leu
            165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
            195                 200                 205

Arg Gly Pro Ser Glu Tyr Pro Thr Lys Asn Tyr Val
    210                 215                 220
```

<210> SEQ ID NO 4
<211> LENGTH: 15
<212> TYPE: PRT
<213> ORGANISM: Artificial Sequence
<220> FEATURE:
<223> OTHER INFORMATION: Linker

<400> SEQUENCE: 4

```
Gly Gly Gly Gly Ser Gly Gly Gly Gly Ser Gly Gly Gly Gly Ser
1               5                   10                  15
```

<210> SEQ ID NO 5
<211> LENGTH: 19
<212> TYPE: PRT
<213> ORGANISM: Artificial Sequence
<220> FEATURE:
<223> OTHER INFORMATION: Signal peptide

<400> SEQUENCE: 5

```
Met Asp Trp Ile Trp Arg Ile Leu Phe Leu Val Gly Ala Ala Thr Gly
1               5                   10                  15

Ala His Ser
```

<210> SEQ ID NO 6
<211> LENGTH: 231
<212> TYPE: PRT
<213> ORGANISM: Artificial Sequence
<220> FEATURE:
<223> OTHER INFORMATION: human IgG1 Fc fragment

<400> SEQUENCE: 6

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65              70                  75                  80

Asn Ser Thr Tyr Arg Val Val Ser Val Leu Thr Val Leu His Gln Asp
            85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
```

```
                145                 150                 155                 160
Ile Ala Val Glu Trp Glu Ser Asn Gly Gln Pro Glu Asn Asn Tyr Lys
                    165                 170                 175

Thr Thr Pro Pro Val Leu Asp Ser Asp Gly Ser Phe Phe Leu Tyr Ser
                    180                 185                 190

Lys Leu Thr Val Asp Lys Ser Arg Trp Gln Gln Gly Asn Val Phe Ser
                    195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 7
<211> LENGTH: 68
<212> TYPE: PRT
<213> ORGANISM: Artificial Sequence
<220> FEATURE:
<223> OTHER INFORMATION: human CD28 (TM + ic)

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Ala Tyr Ala Ala Ala Arg Asp Phe Ala
        50                  55                  60

Ala Tyr Arg Ser
65

<210> SEQ ID NO 8
<211> LENGTH: 113
<212> TYPE: PRT
<213> ORGANISM: Artificial Sequence
<220> FEATURE:
<223> OTHER INFORMATION: human CD3-zeta (ic)

<400> SEQUENCE: 8

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
                20                  25                  30

Tyr Asp Val Leu Asp Lys Arg Arg Gly Arg Asp Pro Glu Met Gly Gly
            35                  40                  45

Lys Pro Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```